US011723797B2

(12) United States Patent
Stowe

(10) Patent No.: US 11,723,797 B2
(45) Date of Patent: Aug. 15, 2023

(54) NON-GRAVITATIONAL FLUID DELIVERY DEVICE FOR OPHTHALMIC APPLICATIONS

(71) Applicant: Twenty Twenty Therapeutics LLC, South San Francisco, CA (US)

(72) Inventor: Timothy Stowe, Alameda, CA (US)

(73) Assignee: TWENTY TWENTY THERAPEUTICS LLC, South San Francisco, CA (US)

( * ) Notice: Subject to any disclaimer, the term of this patent is extended or adjusted under 35 U.S.C. 154(b) by 0 days.

(21) Appl. No.: 18/059,172

(22) Filed: Nov. 28, 2022

(65) Prior Publication Data

US 2023/0089768 A1 Mar. 23, 2023

Related U.S. Application Data

(63) Continuation of application No. 15/931,482, filed on May 13, 2020, now Pat. No. 11,510,809.

(60) Provisional application No. 63/024,373, filed on May 13, 2020, provisional application No. 62/847,693, filed on May 14, 2019.

(51) Int. Cl.
*A61F 9/00* (2006.01)
*A61L 2/26* (2006.01)
*A61L 2/10* (2006.01)
*A61B 5/11* (2006.01)

(52) U.S. Cl.
CPC .............. *A61F 9/0008* (2013.01); *A61L 2/10* (2013.01); *A61L 2/26* (2013.01); *A61B 5/1103* (2013.01); *A61F 2210/0071* (2013.01); *A61L 2202/11* (2013.01); *A61L 2202/24* (2013.01)

(58) Field of Classification Search
CPC ............ A61F 9/0008; A61F 2210/0071; A61F 9/0026; A61L 2/10; A61L 2/26; A61L 2202/11; A61L 2202/24; A61B 5/1103
See application file for complete search history.

(56) References Cited

U.S. PATENT DOCUMENTS

| 8,545,463 | B2 * | 10/2013 | Collins, Jr. | .......... A61M 11/065 604/300 |
| 10,073,949 | B2 * | 9/2018 | Ballou, Jr. | ............. G16H 40/63 |
| 10,154,923 | B2 * | 12/2018 | Hunter | ................ A61B 5/4839 |
| 11,173,510 | B2 * | 11/2021 | Sinha | ................... G02B 6/4415 |
| 11,298,537 | B2 * | 4/2022 | Gutierrez | ............. A61N 1/3787 |

(Continued)

OTHER PUBLICATIONS

European Patent Office, Extended Search Report for EP20805378.5, dated May 11, 2023, 8 pages.

*Primary Examiner* — David A Vanore
(74) *Attorney, Agent, or Firm* — Haynes and Boone, LLP

(57) ABSTRACT

A fluid dispensing device includes a cartridge comprising a housing and a head coupled to the housing. The housing forms a first chamber configured to accommodate a fluid; and the head includes a nozzle; and an elastomeric wall that is spaced from the nozzle to form a holding chamber. The holding chamber is in fluid communication with the first chamber and configured to accommodate a portion of the fluid; and the nozzle forms one or more openings to eject the portion of the fluid from the holding chamber. The one or more openings form an oblong shape such that a length of the oblong shape is greater than a width of the oblong shape. The one or more openings can include two parallel slots that together form the oblong shape.

19 Claims, 20 Drawing Sheets

(56) References Cited

U.S. PATENT DOCUMENTS

| | | | |
|---|---|---|---|
| 11,376,432 B2* | 7/2022 | Gutierrez | A61N 1/36034 |
| 2004/0204674 A1* | 10/2004 | Anderson | A61F 9/0008 |
| | | | 604/66 |
| 2005/0000591 A1* | 1/2005 | Py | B65D 83/62 |
| | | | 141/314 |
| 2005/0029307 A1* | 2/2005 | Py | B05B 11/0054 |
| | | | 222/386 |
| 2005/0261641 A1 | 11/2005 | Warchol et al. | |
| 2009/0149829 A1 | 6/2009 | Collins | |
| 2010/0022971 A1* | 1/2010 | Marx | A61F 9/0026 |
| | | | 604/302 |
| 2013/0079599 A1* | 3/2013 | Holmes | A61B 8/483 |
| | | | 600/300 |
| 2013/0085460 A1* | 4/2013 | Voss | A61F 9/0008 |
| | | | 604/290 |
| 2014/0213989 A1* | 7/2014 | Kelly | A61F 9/0008 |
| | | | 604/296 |
| 2015/0018781 A1* | 1/2015 | Rinderknect | A61F 9/0026 |
| | | | 604/298 |
| 2018/0193190 A1* | 7/2018 | Ajaelo | G16H 20/13 |
| 2021/0353458 A1* | 11/2021 | Stowe | A61F 9/0017 |
| 2022/0031506 A1* | 2/2022 | Lee | A61N 1/36046 |
| 2022/0226156 A1* | 7/2022 | Lee | A61F 2/14 |

* cited by examiner

NON-GRAVITATIONAL FLUID DELIVERY DEVICE FOR OPHTHALMIC APPLICATIONS

CROSS-REFERENCE TO RELATED APPLICATIONS

This application is a continuation of U.S. application Ser. No. 15/931,482, filed May 13, 2020, which claims the benefit of the filing date of, and priority to, U.S. Provisional Application No. 62/847,693, filed May 14, 2019, and U.S. Provisional Application No. 63/024,373, filed May 13, 2020, the entire disclosures of which are incorporated herein by reference.

TECHNICAL FIELD

The present disclosure relates in general to a device to deliver ophthalmic drugs to an eye of a user. The device allows for the non-gravitational delivery of viscous ophthalmic drugs to the eye using one or more micro-streams.

BACKGROUND

Many eye-drop medications and artificial tear formulations with increased formulation viscosity (e.g., 50 centipoise (cps) to 200 cps) have been shown to have longer residence time, better mucosal adhesion (adhesion to mucin cells), and improved corneal hydration. This is important for dry eye diseases but also important for other drug delivery applications where higher concentrations and longer residence time improve drug delivery efficacy.

Dispensing higher viscosity fluids (e.g., fluids having a viscosity of between 50 cps to 200 cps) from a conventional eye dropper is not ideal for a number of reasons. First, the dose volume for a conventional eye dropper varies. The dose volume can range anywhere from 30 to 65 µL, with a repeatability of about +/−5 µL or about +/−10% of standard deviation. The tilt angle range, which people use during application using a conventional eye dropper, can have a measurable impact on drop volume by up to an additional 10%. To account for partial misses of fluid delivery to the eye, an excess of fluid is typically delivered to the eye using a conventional eye dropper. When the dose volume varies and there is an excess fluid applied to the eye, the excess fluid sometimes takes several minutes to drain from the eye, which can temporarily lead to a non-uniform tear layer that causes blurring due to spherical and comb aberrations. A further nuisance is that sometimes the excess viscous drop volume partially misses the eye during application and then gets stuck in the eyelashes, which leads to crusting as the drop dries out.

Second, the shape and size of a drop resulting from a conventional eye dropper results in reduced uniform spreading of the drop over the eye. Generally, a conventional shape and size of a 50 µL drop resulting from a conventional eye dropper is a semi-sphere having a diameter approximately 5 mm. When a 5 mm diameter sphere contacts the eye, there is approximately about 2 mm of margin on either side of the drop between the drop and the eyelid. As such, it is often difficult to hit the eye without a portion of the drop landing or splashing outside of the eye. When the drop is of a highly viscous fluid, the drop that hits the corneal surface can be approximately 2-3 mm in height as measured normal to the surface of the cornea. The wiping action of the human eyelid does not do well to force the uniform spreading of such a tall perturbation given the eyelid itself is only approximately 3-4 mm thick. As such, uniform spreading becomes more challenging with high viscosity formulations.

Accordingly, for high viscosity formulations, it is preferred to dispense smaller, uniform doses across the eye and allow the eyelids to spread the small drops uniformly in the vertical direction (e.g., between eyelids). Using smaller doses reduces or eliminates problems associated with short term blurring and can allow for even higher viscosity formulations that are more effective in terms of their residency time and moisture retention, and therefore, are more pleasing to the end user.

Moreover, with conventional reusable eye drop systems, preservatives are often included in the dispensed fluid to prevent the growth of bacterial or viral germs. These preservatives may result in damage and corneal sensitization over time for those people that regularly use the drops. While a filter may be used to reject the preservative before it reaches the eye of the user, the filter may not be applicable to all types of fluids/formulations. Reusable eye drop systems that do not include preservatives often require built-in filters and unidirectional valves, but this is complex and adds significant cost to the packaging of the reusable eye drop system.

Finally, conventional reusable eye drop systems do not remind the user to take eye drop medication, help the user efficiently guide eye drops effectively into their eyes without blink interference, and verify the user is taking the medication at the prescribed dosage.

Thus, a system for applying smaller viscous drop sizes evenly across the eye with a horizontal non-gravitational delivery and sterilization capability that also reminds the user to take eye drop medication, helps the user efficiently guide eye drops effectively into their eyes without blink interference, and verifies the user is taking the medication at the prescribed dosage is needed.

DETAILED DESCRIPTION

Disclosed herein is one example of a non-gravitational dropper device and/or sprayer device that delivers a fluid to a patient or user. However, neither the term "spray", "sprayer", "drop", or "dropper" are limiting, as the fluid that is dispersed from the device may be considered a "stream", "micro-stream", or "sheet" of fluid. Generally, the fluid dispersed from the device includes a pulsed continuous stream of liquid. Generally, the device delivers a fluid to the eye of a patient, but the device could be used for other applications, such as to deliver viscous fluid medications to the nose or mouth in other applications. In one embodiment, the device is configured to deliver a viscous ophthalmic drug to the eye of the patient via a nozzle with an array of openings forming an oblong shape or a slit-like opening forming an oblong shape such that the delivery of the fluid via the nozzle results in an oblong application of the fluid across a horizontal portion of the eye, which improves the application of the fluid to the eye. Generally, the delivery of the fluid via the array of openings allows for multiple droplet streams with extended tails to contact the eye, with the streams contacting different locations in the eye.

Figure 1:
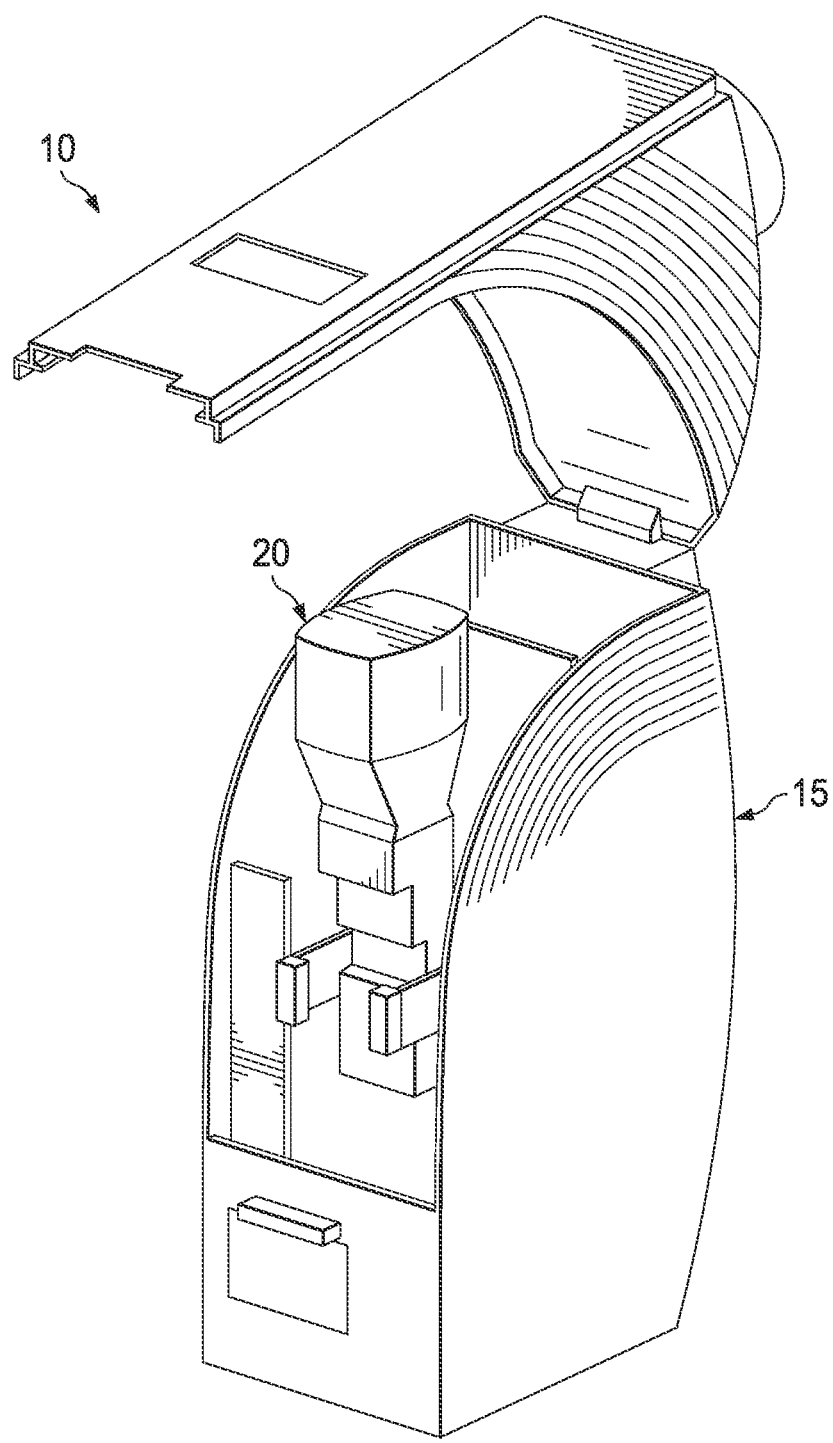
FIG. 1 is a perspective view of an example non-gravitational fluid delivery device in accordance with at least one embodiment of the present disclosure, the non-gravitational fluid delivery device system including a cartridge housed within an applicator.

FIG. 1 illustrates an embodiment of a fluid delivery device that is referenced and designated by the numeral 10. In some embodiments, the device 10 includes an applicator 15 and a cartridge 20 that is removably positioned within the applicator 15.

Figure 2:
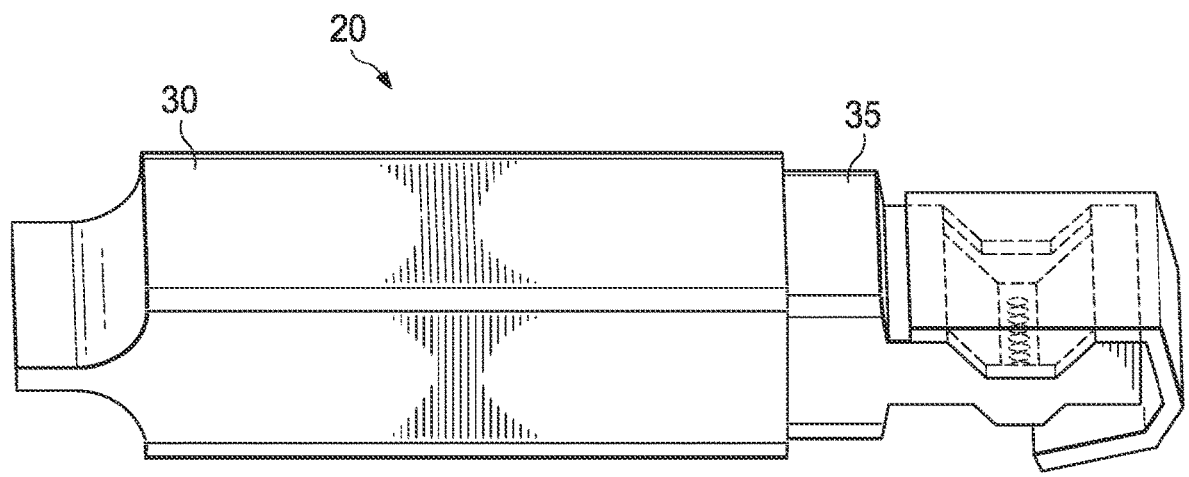
FIG. 2 is a perspective view of the cartridge of FIG. 1, in accordance with at least one embodiment of the present disclosure.

FIG. 2 illustrates an embodiment of the cartridge 20. As illustrated, the cartridge 20 includes a housing 30 and a head 35 that is attached to the housing 30. In some embodiments, the cartridge 20 is about 14 mm wide×14 mm long×7 mm thick, however, the dimensions may vary.

Figure 3:
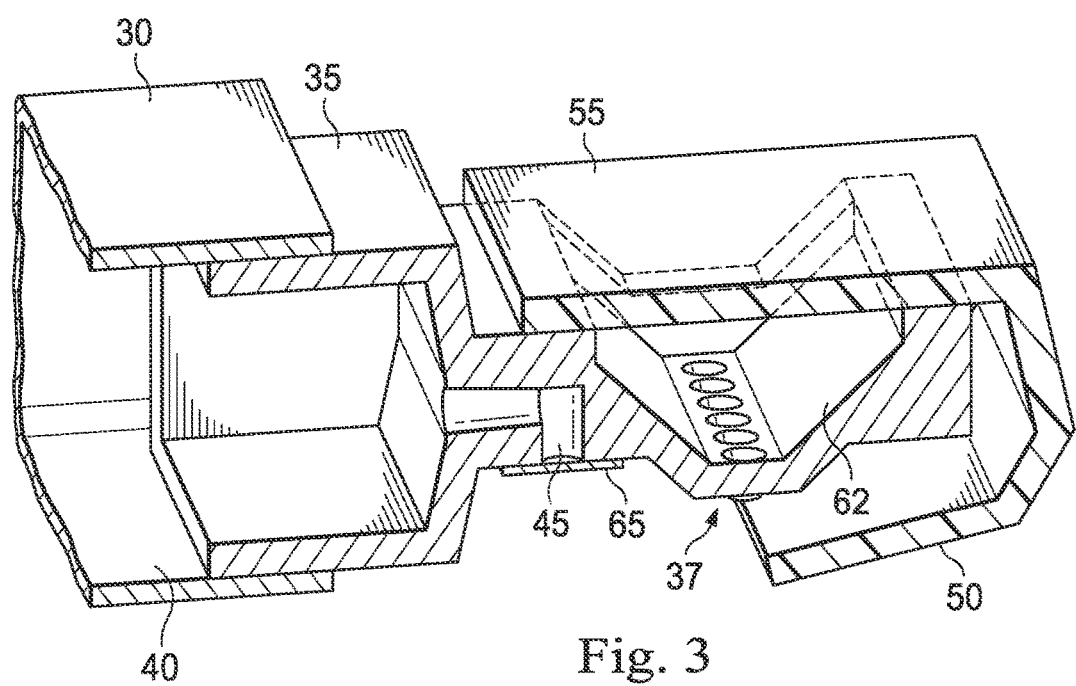
FIG. 3 is a perspective cutaway view of the cartridge of FIG. 1, in accordance with at least one embodiment of the present disclosure.

Generally, and as illustrated in the cutaway view in FIG. 3, the housing 30 is a fluid reservoir or forms a chamber 40 in which a viscous drug or viscous fluid (not illustrated in FIG. 3) is accommodated. In some embodiments, the viscous fluid is aseptically dispensed before the head 35 is heat sealed or coupled to the housing 30. In some embodiments, the housing 30 is a blow-fill-seal package container.

Figure 4:
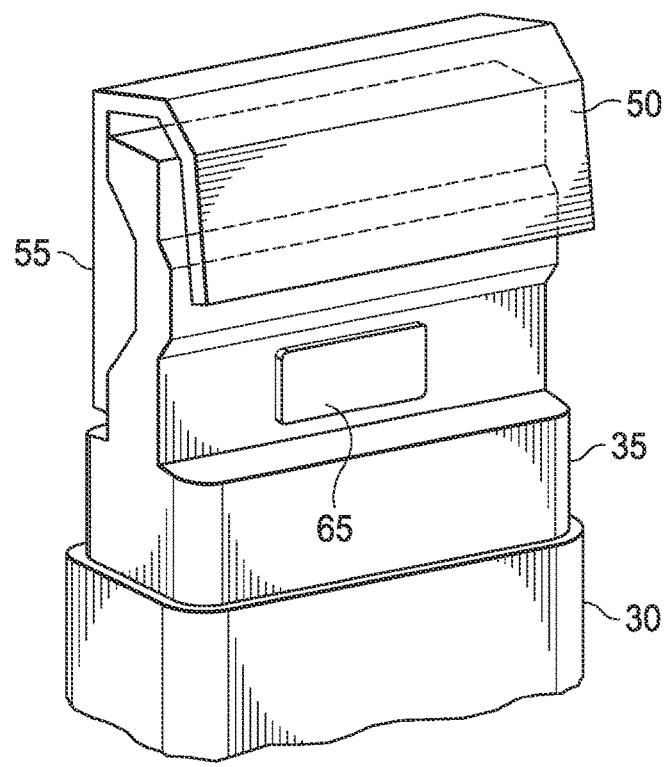
FIG. 4 is a perspective view of a portion of the cartridge of FIG. 1, in accordance with at least one embodiment of the present disclosure.

As illustrated, the head 35 is coupled to the housing 30 to dispense the viscous fluid from the chamber 40. Generally, the head 35 is at least temporarily in fluid communication with the chamber 40 and forms a nozzle 37 and an air entry port 45. The head 35 also includes a cap 50 and a wall 55 that is movable relative to the nozzle 37. The head 35 forms a holding chamber 62 that is in fluid communication with the chamber 40 and that is positioned between the nozzle 37 and the wall 55. In some embodiments, the air entry port 45 is positioned between the nozzle 37 and the housing 30 as illustrated in FIGS. 3 and 4. In some embodiments, the air entry port 45 is a sterile air filtered air entry port. A filter 65 may be positioned over the air entry port 45. In some embodiments, the filter 65 is made from polypropylene porous material with 0.1 µm-0.2 µm passages. The filter 65 can be welded directly to the head 35 when the head 35 is also molded from polypropylene. In some embodiments, the wall 55 is a membrane or elastomeric wall that is "squeezable" or flexible enough to deform in response to a striking force being applied to the wall 55.

Figure 5:
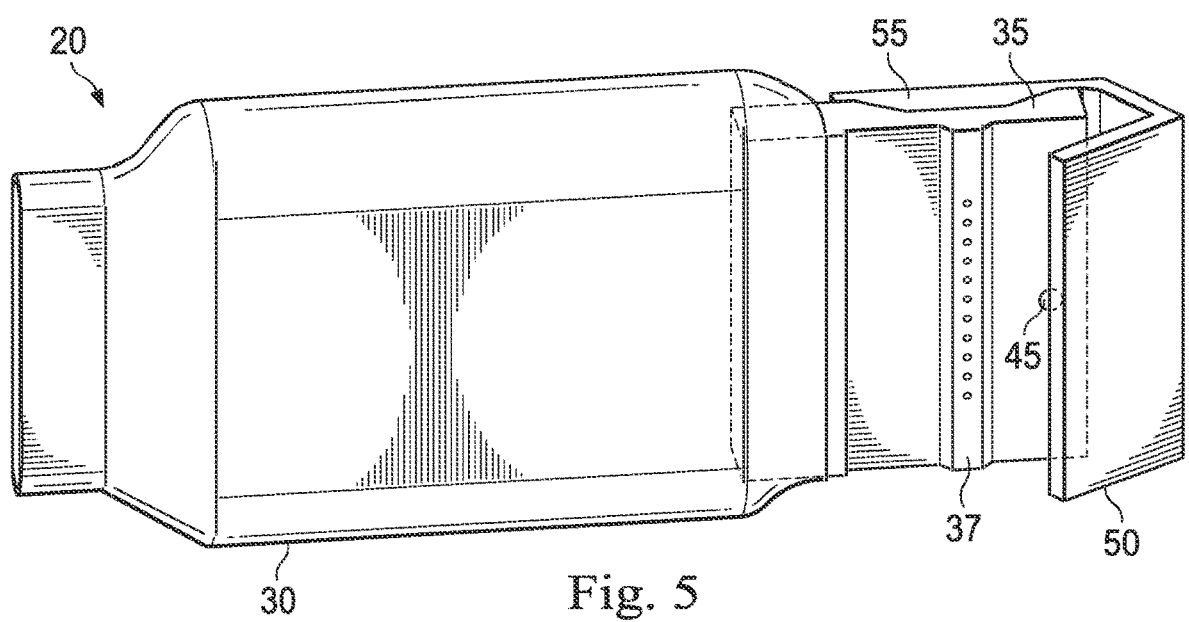
FIG. 5 is another perspective view of the cartridge of FIG. 1, in accordance with at least one embodiment of the present disclosure.

FIG. 5 is a perspective view of the device 10 and illustrates an embodiment of the head 35 in which the nozzle 37 is positioned between the air entry port 45 and the housing 30. In some embodiments, the cap 50 protects the air entry port 45 from debris during loading of the cartridge 20 into the applicator 15. In some embodiments, the air entry port 45 is on the opposite size of the nozzle 37 (illustrated in FIGS. 26 and 27).

Figure 6:
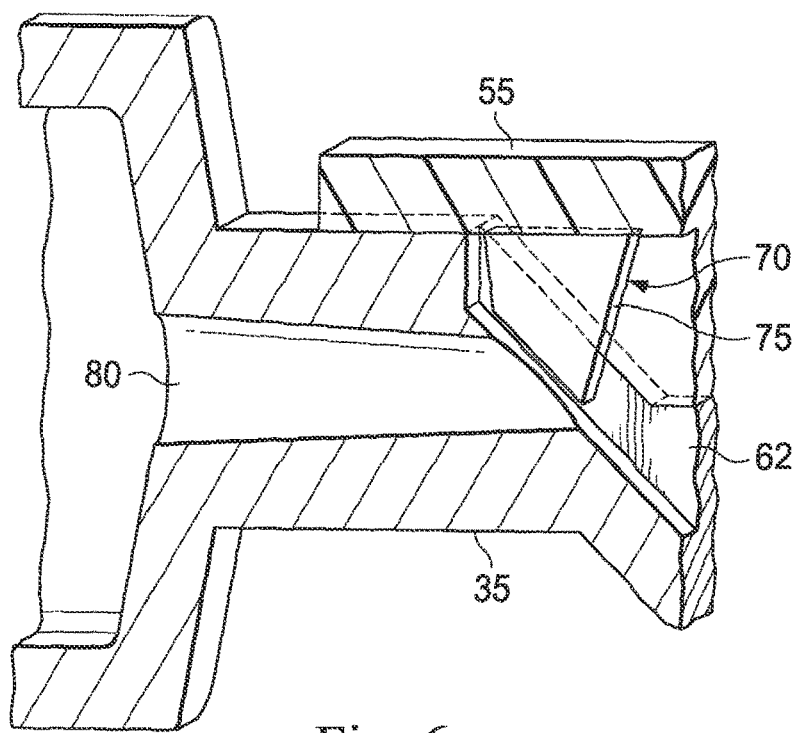
FIG. 6 is a cross-sectional view of a portion of the cartridge of FIG. 1, in accordance with at least one embodiment of the present disclosure.

FIG. 6 is a partial cross-sectional view of the head 35. As illustrated, a valve 70 is formed or positioned within the head 35 such that when direct mechanical impact occurs on the wall 55, which induces positive displacement that ejects fluid from the nozzle 37, the valve 70 is moved into a closed position such that the fluid does not return from the head 35 into the chamber 40. One example valve 70 includes an arm 75 that is coupled to the wall 55 such that movement of the wall 55 also moves the arm 75. Downward movement of the wall 55 moves the arm 75 across a passage 80 that extends between the chamber 40 and the head 35. As such, the arm 75 fluidically isolates the holding chamber 62 from the chamber 40, thus making the nozzle 37 the only outlet for the fluid. The arm 75 and the passage 80 are only one example of the valve 70 and may be replaced with many different examples of elastomeric one-way valves.

Figure 7:
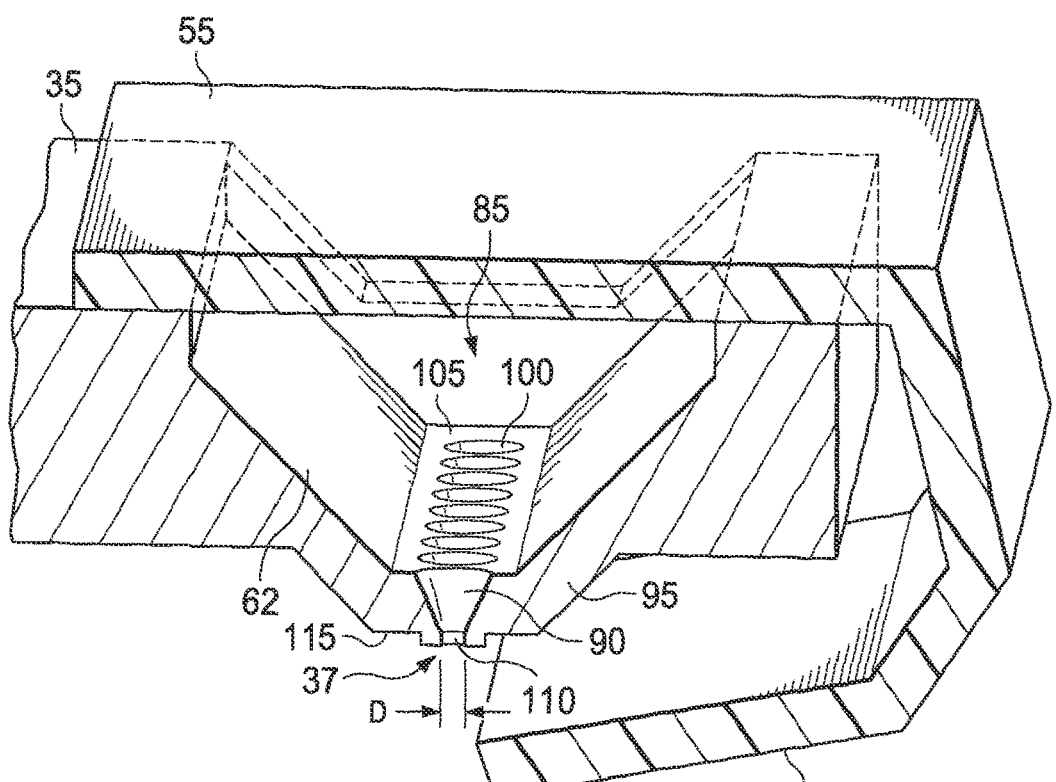
FIG. 7 is a perspective cutaway view of a portion of the cartridge of FIG. 1, in accordance with at least one embodiment of the present disclosure, the portion of the cartridge of FIG. 1 including a nozzle having openings.

FIG. 7 is a partial perspective cutaway view of one embodiment of the head 35. As illustrated, the nozzle 37 includes an array of openings 85. In some embodiments, the cap 50 and the wall 55 are coupled together or formed together. Generally, the purpose of the wall 55 is to facilitate easy squeeze out of the fluid through the nozzle 37 and to allow easy self-contained capping of the nozzle 37, via the cap 50, after a jetting event. FIG. 7 also illustrates a conical shape of each opening in the array of openings 85. As illustrated, an opening 90 of the array of openings 85 includes a conical shape as it extends through a wall 95 of the nozzle 37. That is, an opening 100 in the interior surface 105 of the head 35 is larger than an opening 110 in the exterior surface 115 of the head 35.

Generally, a target diameter D of the opening 110 is based on the liquid viscosity, delivery speed, surface tension, and density of the fluid to be dispersed. Generally, the target diameter D must be large enough to overcome hydraulic losses from the viscous force, but small enough that the stream, or ejection of fluid, will pinch off into a single drop due to surface tension forces. In some embodiments, the target slit width or diameter of a nozzle is 100-300 microns, a delivery speed is approximately 1.5-3 meters/second (m/s), liquid viscosity (µ) is between about 1 cp-500 cp, surface tension (σ) is between about 40-72 dynes/cm, and density (ρ) is approximately that of water or about 1 gm/cc. Generally, the ejection velocity or speed needs to be low enough so as to be well tolerated in terms of the eye sensation, but high enough to traverse the target distances between 10-25 mm without being substantially deflected by gravity or cross winds. Speeds below 3 m/s are much lower and a small fraction of the speed of raindrops, gentle shower heads, eye washes, and established regulations for water jet speeds at water parks and for toy water guns. Speeds above 1 m/s ensure only a sub millimeter deflection due to gravity of the nozzle aim over aiming distances up to 20 mm. In some embodiments, 1.5 m/s is an optimal speed, but with some viscous materials, the initial velocity may decrease over the trajectory due to the viscous drag of the microstream tail such that initial ejection speeds of 3 m/s are more ideal as velocity on impact to the eye is lower. The optimal nozzle diameter D is between 100-300 µm, with the exact dimension depending upon the influence of nozzle surface tension, viscosity of the medium, volume of ejected fluid, and sensitivity to contamination. Target volume may be as low as 8 µL to be fully effective, as this value is approximately the maximum amount of tear fluid an eye can hold without immediate drainage. Volumes in the range of 10 µL-15 µL are more ideal to account for some possibilities for loss. Generally, openings having circular shapes require diameters of 100-300 µms.

Figure 8:
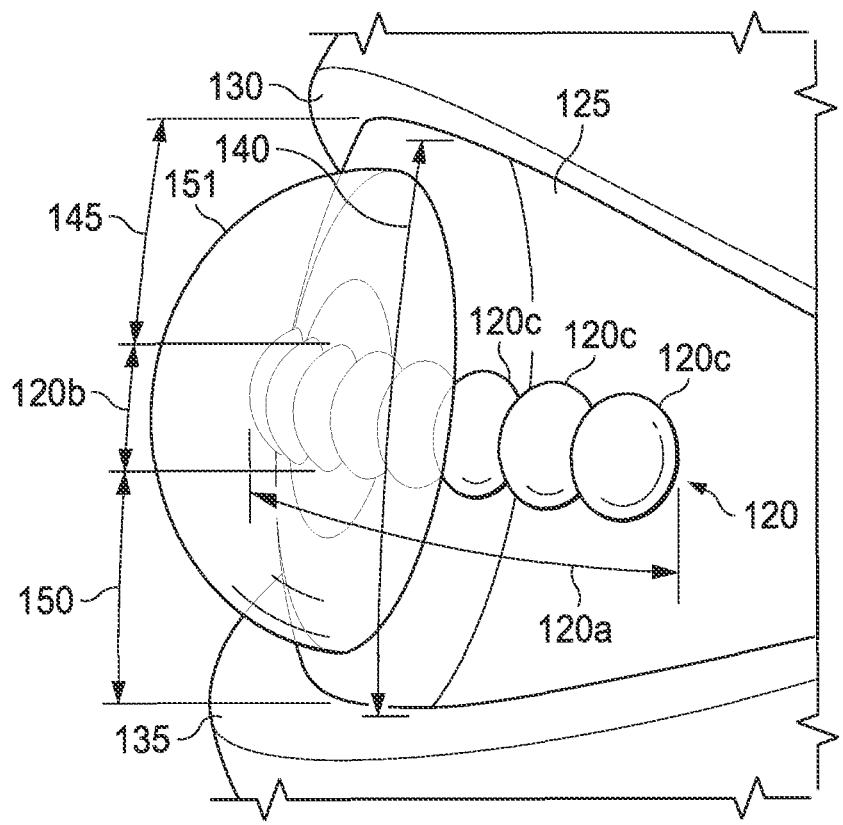
FIG. 8 is a diagrammatic perspective view of an eye, in accordance with an embodiment of the present disclosure.

FIG. 8 illustrates an array of microdroplets 120 on an eye 125 after they have been delivered through the nozzle 37 of the device 10 from FIG. 1. The array 120 generally defines a width 120a and a height 120b. As illustrated, the array 120 is composed of small spherical droplets 120c. As the array of openings 85 is arranged linearly on one axis, the linear arrangement of the openings 85 results in the oblong shape of the array of microdroplets 120 when collectively merged together. The eye 125 includes an upper eyelid 130 and a lower eyelid 135 and, when opened, exposes a surface of the eye 125 that has a dimension 140 measured—in the same direction as the height 120b—between the upper and lower eyelids 130 and 135. Generally, the exposed cornea and sclera regions are elliptical in shape. Due to the height 120b relative to the dimension 140, a clearance 145 is formed between the array of the microdroplets 120 and the upper eyelid 130, and a clearance 150 is formed between the array of microdroplets 120 and the lower eyelid 135. The array of microdroplets 120 allows for a more uniform delivery of fluid in the horizontal direction (i.e., the direction in which the width 120a of the array 120 is measured in FIG. 8) across the cornea. The uniform spreading of these microdroplets in the vertical direction (i.e., the direction in which the height 120b of the array 120 is measured in FIG. 8) is facilitated quickly after a few blinks of the eyelids 130 and 135, which act like windshield wipers across the surface of the eye 125. FIG. 8 also illustrates a conventional droplet 151 and its size compared to the array of microdroplets 120.

Figures 9A, 9B:
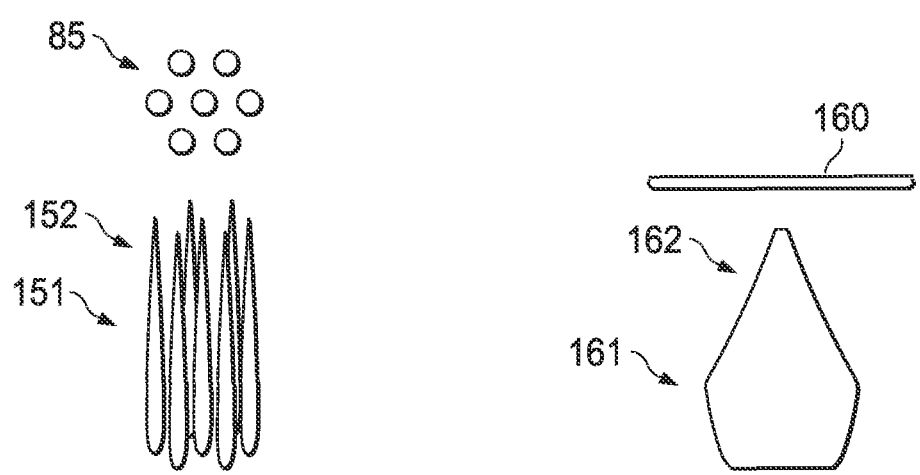
FIG. 9A is a diagrammatic of the opening(s) of the nozzle and resulting drop shapes, according to an example embodiment.
FIG. 9B is a diagrammatic of the opening(s) of the nozzle and resulting drop shape, according to another example embodiment.

In practice, viscous fluids above 100 cps typically have a "tail" upon ejection because the stream fails to quickly pinch off, due to surface tension, or separate from the nozzle 37. FIG. 9A illustrates fluid streams 151 that are formed by a nozzle having the plurality of circular openings 85. As illustrated, each of the fluid streams has a "tail" portion 152 that, in some embodiments, never detach from the nozzle 37 and at least a small portion of the tail remains on the nozzle 37 as residue. In some embodiments, each of the streams coalesce into a single microstream after exiting the nozzle 37. However, the number of tails formed using the plurality of circular openings 85 can lead to excess waste or contamination. When the plurality of openings 85 are arranged in a horizontal or linear array to form an oblong shape, typically the streams have some overlap by the time they reach the eye 125 and form a continuous oval-like film very similar in shape to the oval eye opening between the eyelids. The micro-stream formed is stable to air flow. In some embodiments, dust or debris may clog one or more openings as the size of each opening is small (e.g., 100-200 μm).

Figure 10:
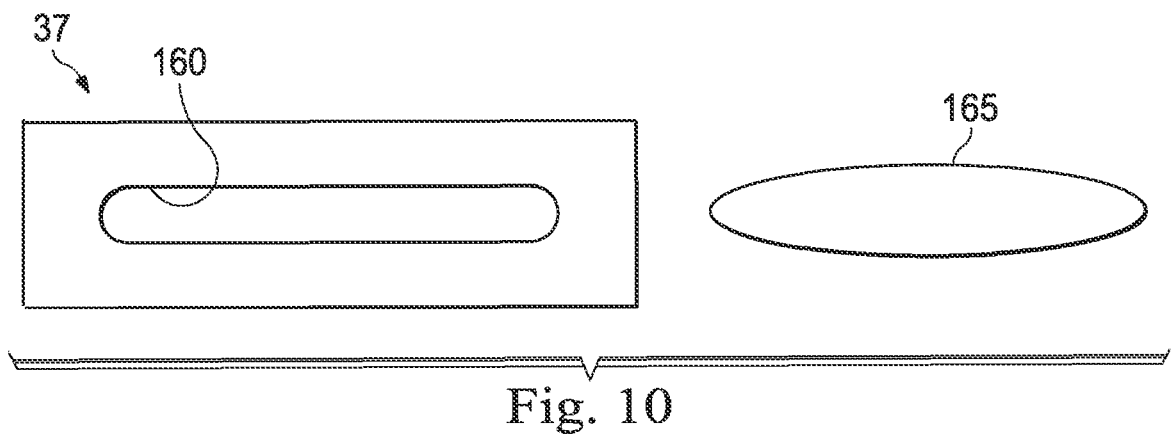
FIG. 10 is a diagrammatic illustration of the opening of the nozzle of FIG. 9B and a resulting drop footprint, in accordance with another embodiment of the present disclosure.

In some embodiments and as illustrated in FIG. 9B, the nozzle 37 includes an oval or stadium shaped opening 160 in the nozzle 37, which facilitates pinch off while preserving the cross-sectional area and thus generally maintaining or reducing the cross-sectional impedance for flow. As illustrated, generally one microstream 161 having one tail portion 162 is formed by the opening 160. When each tail portion potentially creates residue on the nozzle 37, reducing the number of tail portions created in each ejection reduces the volume of residue remaining on the nozzle 37 after each ejection. As such, the nozzle 37 including one linearly extended opening 160 may reduce the volume of residue when compared to the volume ejected as compared to a nozzle 37 having three or more circular openings. For example, instead of having a nozzle 37 with openings having a 300 μm diameter, the nozzle 37 can include only one opening that is 200 μm×8000 μm (8 mm) along the longitudinal axis. In some embodiments, a slit-like opening has a more active ejection area than the plurality of openings 85, and therefore, an actuation energy needed to deliver the fluid is reduced. Moreover, a slit-like opening allows for a microstream to coalesce quicker than the plurality of openings 85, and thus, forms a much more targeted delivery of liquid less much less susceptible to external air currents. As such, instead of having the plurality of openings 85 as illustrated in FIG. 7, in some embodiments the nozzle 37 includes one opening that forms a ribbon shaped "sheet" micro-stream instead of a cylindrically shaped micro-stream. This "sheet" like micro-stream is therefore advantageous in some embodiments. For example, and as illustrated in FIG. 10, the plurality of openings 85 may be omitted and one opening 160 is formed in the nozzle 37. As illustrated, the opening 160 has a length much greater than a width and thus forms an oblong shape. The drop footprint 165 associated with the opening 160 is also illustrated in FIG. 10. As illustrated, the opening 160 is a stadium shape. The tail end eventually forms a single viscous tail much smaller than the nozzle 37, and thus dramatically reduces or eliminates residue. The degree to which break up of this liquid micro sheet is reproducible at the tail end of the jet is extremely complex and is affected by lateral airflow, small nozzle shape defects, entrainment of air bubbles at the nozzle exit, or small perturbations due to surface debris. These instabilities arise from a simple thin walled liquid stream and the mathematics characterizing and simulating this behavior is very complex. Regardless, the viscous fluid that is dispersed from the opening 160 generally results in a sheet forming a single tail that is opposite the head of the sheet. In some embodiments, the length of the slit or opening 160 is unlimited and can even be 12 mm long as an example, but the width of the slit requires slightly smaller dimensions typically between 100-250 microns.

Figure 11:
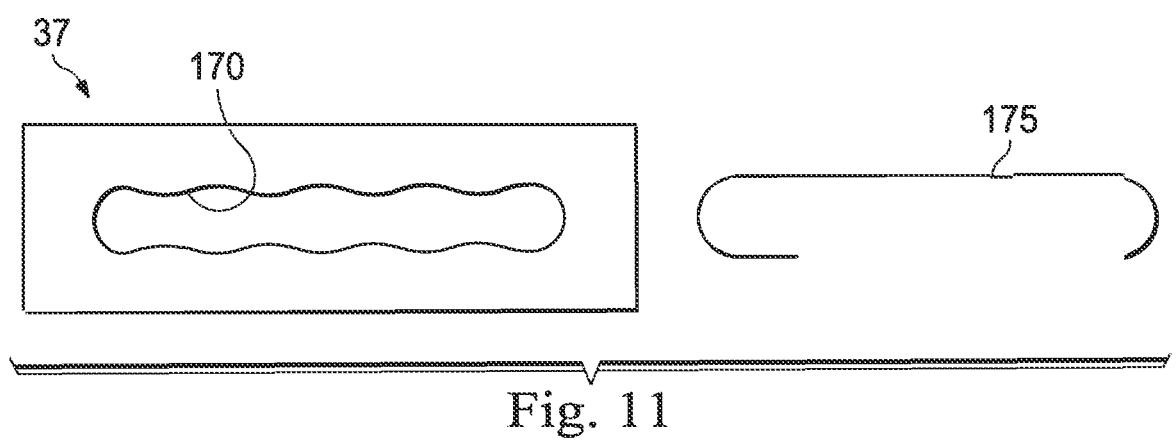
FIG. 11 is a diagrammatic illustration of the opening of FIG. 9B and a resulting drop footprint, in accordance with another embodiment of the present disclosure.

In some embodiments and as illustrated in FIG. 11, the nozzle includes one opening 170 that has an undulating surface to form an undulating stadium shape. When the opening 170 includes an undulating opening, which is configured to match the typical natural spatial frequency owing to air related capillary surface tension instability distances, the tail jetting reproducibility and uniformity can be improved by forcing naturally instabilities to consistently occur, and therefore, be more predictable while at the same time not impacting the overall shape uniformity of the main mass of the micro-stream drop at its head. The drop footprint 175 associated with the opening 170 is also illustrated in FIG. 11. As illustrated in FIG. 11, the generally stadium shape is formed with an undulating surface, but the shape is not limited to the generally stadium shape. For example, the general shape may include a bow-tie shape, a rectangular shape, and the like to improve the tail jetting reproducibility and uniformity of the fluid sheet dispersed from the opening 170. In some embodiments, an undulating surface is defined as a surface having a sinuous or wavelike form. As such, an undulating surface generally has alternating positive and negative radiuses of curvature.

Figure 12:
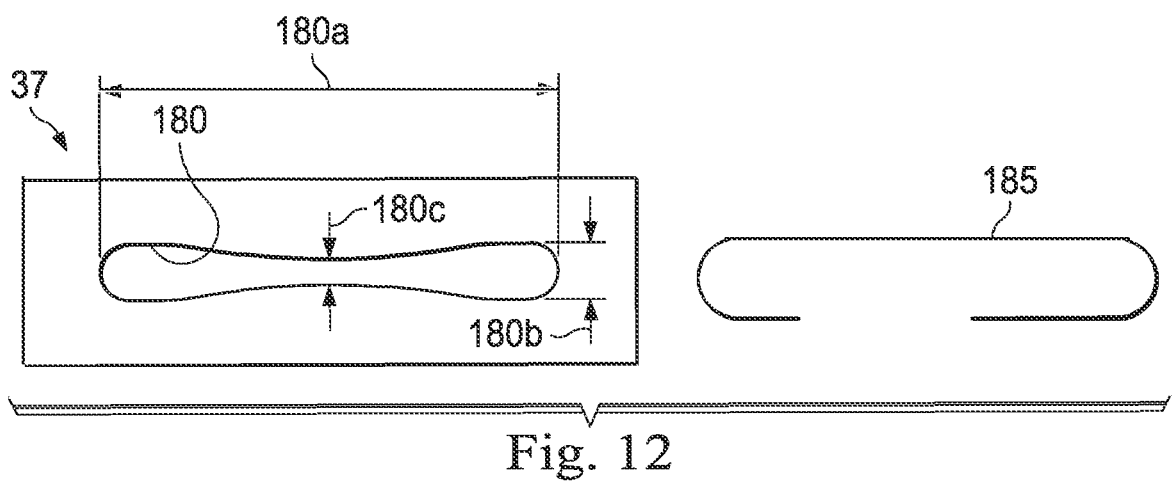
FIG. 12 is a diagrammatic illustration of the opening of FIG. 9B and a resulting drop footprint, in accordance with another embodiment of the present disclosure.

In some embodiments and as illustrated in FIG. 12, the plurality of openings 85 may be omitted and one opening 180 is formed in the nozzle 37. The drop footprint 185 associated with the opening 180 is also illustrated in FIG. 12. As illustrated, the opening 180 forms a bow-tie shape and has a length 180a, a max width 180b, and a minimum width 180c. Because the widths 180b and 180c are small, the ability to pinch off the tail of the drop at the exit of the nozzle 37 is improved. Moreover, because the "sheet" stream that exits the opening 180 is initially connected, inertial forces are larger and provide a stabilizing dynamic which overcomes small amounts of nozzle manufacturing defects or debris and air perturbations. In some embodiments and with the bow-tie shape opening 180, the impedance to jetting at the edge of the slit can be slightly lessened relative to the center, thus creating a more uniform edge profile. Finally, the bow-tie shape delays the coalescence of the "sheet-like" micro-stream into a more cylindrical stream due to surface tension instabilities. By tuning the shape of the nozzle, impact over the eye can generally match the shape of the eye.

Figure 13:
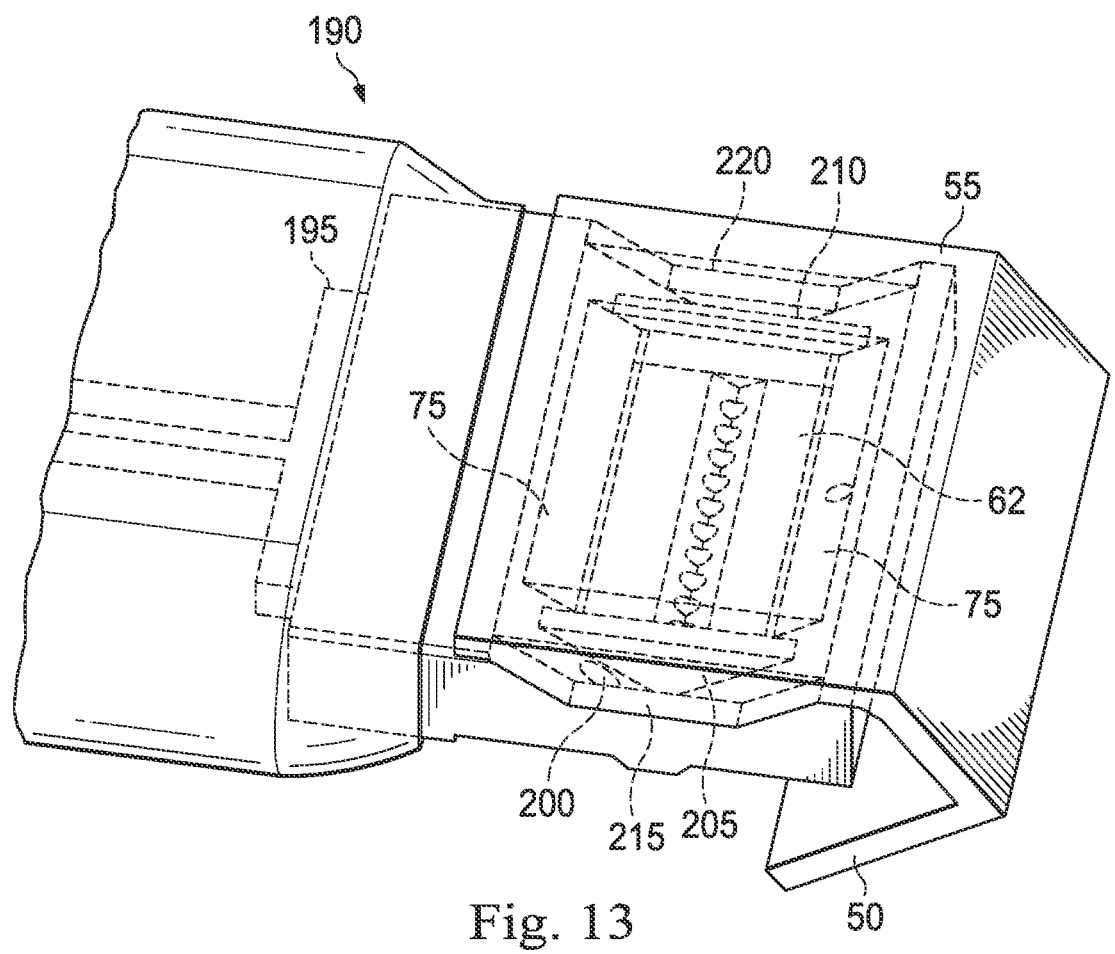
FIG. 13 is a perspective view of the cartridge of FIG. 1, in accordance with another embodiment of the present disclosure.
Figure 14:
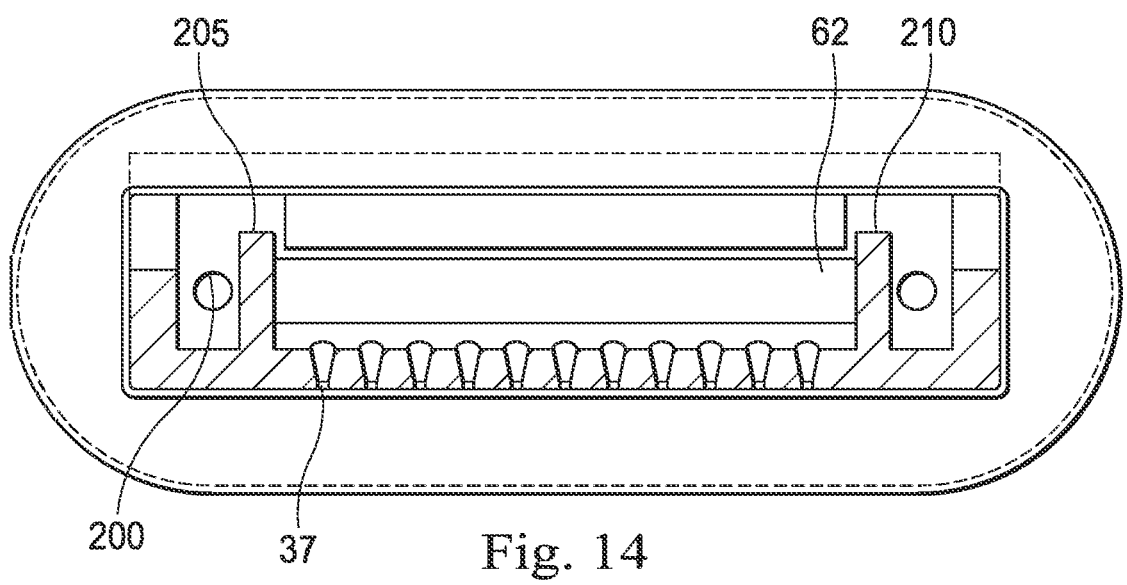
FIG. 14 is a cross-sectional view of the cartridge of FIG. 13, in accordance with at least one embodiment of the present disclosure.

FIGS. 13-14 illustrate another embodiment of the head 35 designated with the reference numeral 190. In some embodiments, the head 190 includes a wicking capillary tube 195 that places the chamber 40 in fluid communication with the holding chamber 62. In some embodiments, the wicking capillary tube 195 does not extend into the holding chamber 62, as it would dampen the fluid ejection. However, the capillary tube 195 helps wick fluid into the holding chamber 62 and acts as mechanical impedance channel, which prevents back flow during a rapid mechanical strike of the wall 55. In some embodiments and when the array of openings 85 is capped before the wall 55 is released from a downward striking position, the wall 55 will provide suction that draws up material through the capillary tube 195 as it returns to its normal position.

The capillary tube 195 may be replaced with a capillary wicking material that provides flow independent of gravity. Typical medical grade capillary wick materials are PET, glycol-modified PET (PETG), or Polyurethane foams made by many different vendors such as Porex, Aquazone® by FXI, PureSorb® by Berkshire, or Capu-Cell® by Foam Sciences.

In some embodiments, the interior surfaces that define the holding chamber 62 have high surface energy materials evaporated on them to facilitate the flow of liquids into the holding chamber 62 and to help prevent the occurrence of trapped bubbles. In some embodiments, air bubble channels 200 are formed in the head 35 and are hydrophobic but the holding chamber 62 is hydrophilic, so the air can escape to the edges and the fluid will fill up the holding chamber 62.

In some embodiments, the head 35 also includes walls 205 and 210 that are not connected to the wall 55, but force flow in one direction and edge walls 215 and 220 that tip down to be more compliant. The result is a geometry that is more uniform to flow along the cross section, as illustrated in FIG. 14. The walls 205, 210, 215, and 220 overcome issues with edge nozzle ejection defects from the deformation of the wall 55 being pinned to a hard edge of the head 35.

In some embodiments, a hydrophilic coating is disposed on the interior surface of the nozzle 37 that ejects the fluid and a Teflon or Teflon-like (e.g., with C-F3 side chain groups) on the exterior surface of the nozzle 37 to reduce leakage from contamination as well as improve uniformity between stream breakups.

Figure 15:
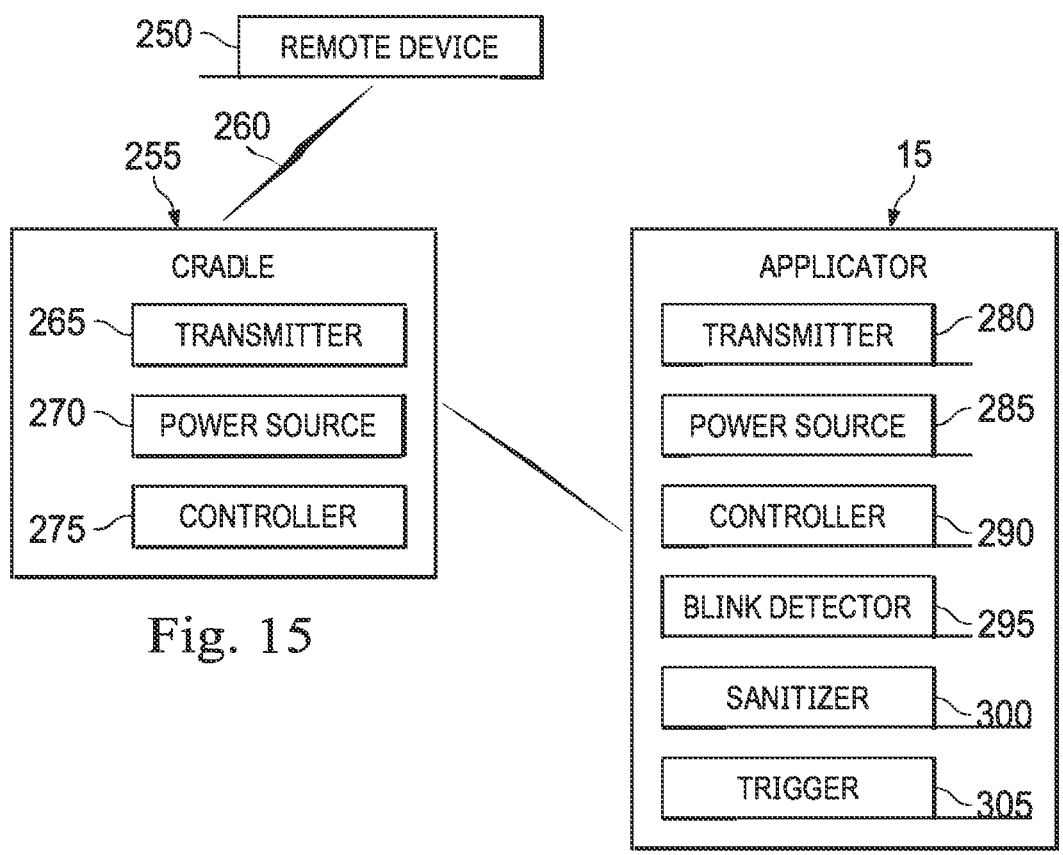
FIG. 15 is a diagrammatic illustration of a cradle, the applicator of FIG. 1, and a controller, the applicator including a sterilizer and a blink detector.

FIG. 15 is a diagrammatic illustration of the applicator 15, a remote device 250, and a cradle 255 that accommodates the applicator 15 all of which are in communication via a network 260. As illustrated, the cradle 255 includes a transmitter 265, a power source 270, and a controller 275. In some embodiments, the applicator 15 includes a transmitter 280, a power source 285, a controller 290, a blink detector 295, a sterilizer 300, and a trigger 305. In some embodiments, the controller 290 is operably coupled to the blink detector 295, the power source 285, the transmitter 280, the sterilizer 300, and the trigger 305.

Figure 16:
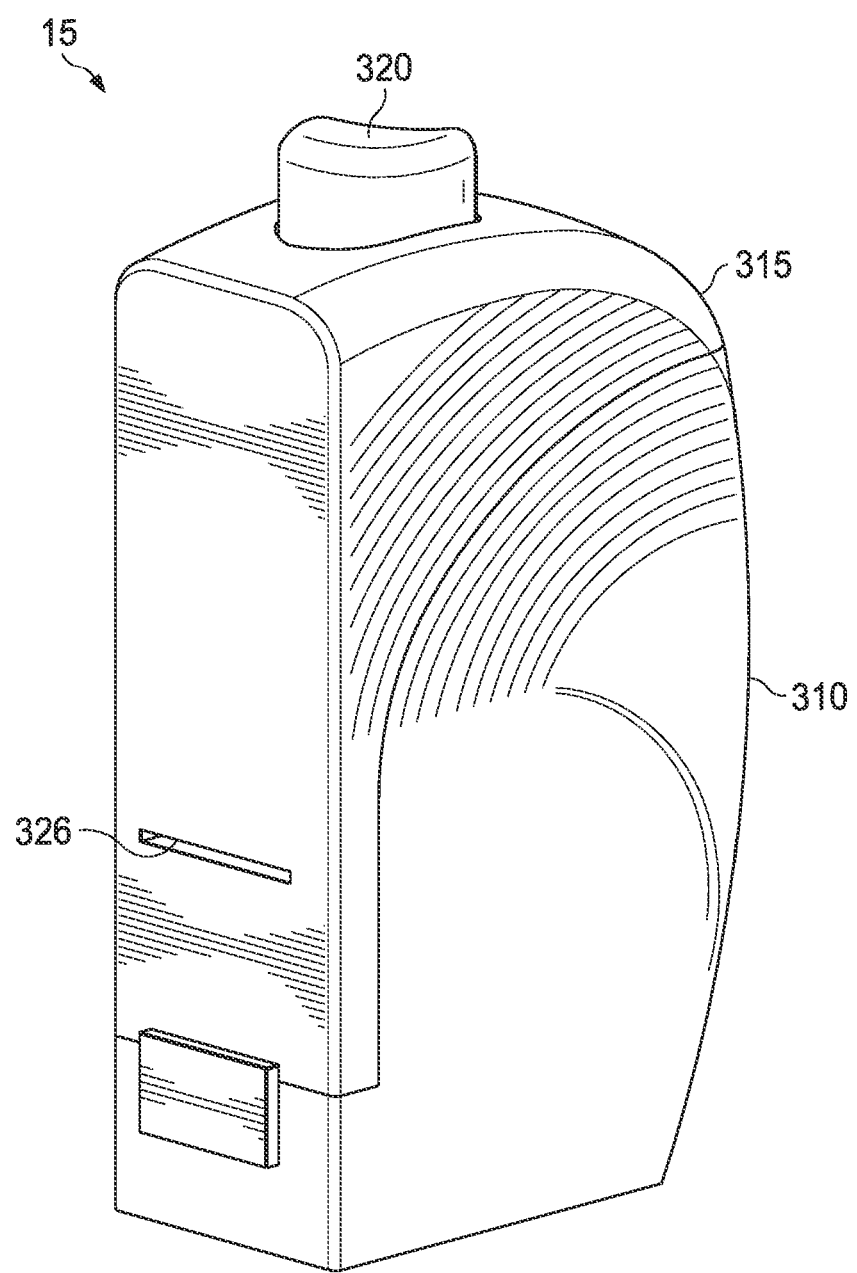
FIG. 16 is a perspective view of the applicator of FIG. 1, in accordance with at least one embodiment of the present disclosure.

Referring to FIG. 16, the applicator 15 includes a housing 310, a cap 315 coupled to and movable relative to the housing 310, a mechanical activation button 320 coupled to a mechanism for opening a dust cover 325 (illustrated in FIG. 23) and for waking up and arming the device 10 for usage. In some embodiments, the applicator 15 includes the sliding dust cover 325, which extends over or across an opening 326 that allows the fluid to exit the housing 310 after exiting the nozzle 37 of the internal cartridge 20. The housing 310 is sized to accommodate the cartridge 20, the transmitter 280, the power source 285, the controller 290, the blink detector 295, the sterilizer 300, and the trigger 305. In some embodiments, the applicator 15 is an "intelligent" applicator 15 that allows for added user convenience such as horizontal non-gravitational spray, visual aiming LEDs, blink detection sensors and triggered dispense upon eyelid opening, as well as full cloud connectivity for compliance monitoring. Because the applicator 15 can be used over and over with replaceable cartridges, the cost to a user is very low and amortized to virtually zero in the case of a long-term user, such as a glaucoma patient.

Figure 17:
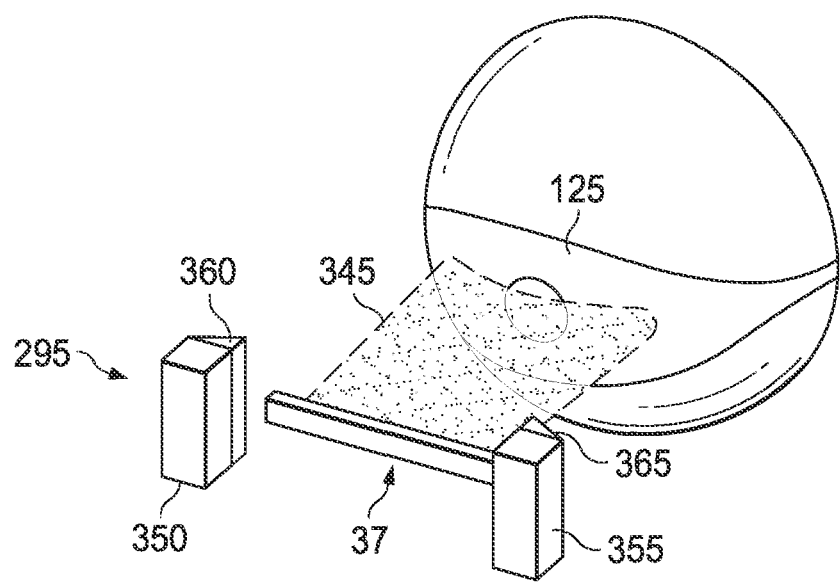
FIG. 17 is a diagrammatic illustration of the blink detector of FIG. 15 and an eye, in accordance with at least one embodiment of the present disclosure.
Figure 18:
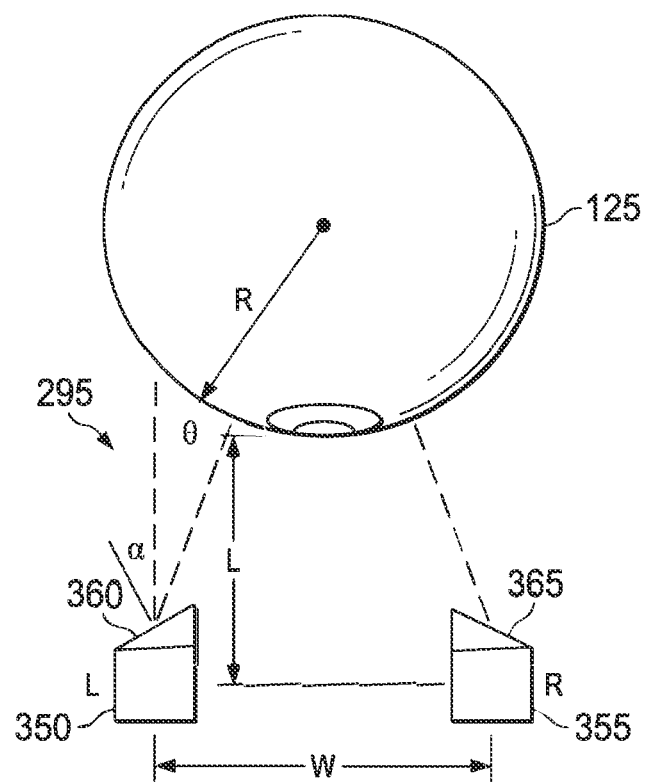
FIG. 18 is another diagrammatic illustration of the blink detector of FIG. 16 and the eye, in accordance with at least one embodiment of the present disclosure.
Figure 19:
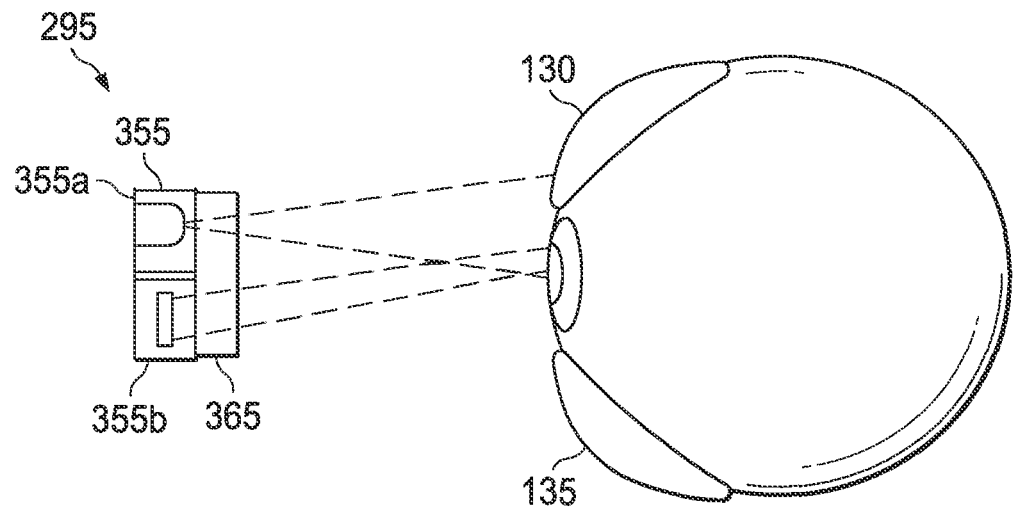
FIG. 19 is yet another diagrammatic illustration of the blink detector of FIG. 16 and the eye, in accordance with at least one embodiment of the present disclosure.

Turning to FIGS. 17-19, an electronic alignment check before or during drug delivery is ideal to align the nozzle 37 with the eye 125. In some embodiments, the blink detector 295 includes one or more reflective optical proximity infrared sensors to detect the face/eye being within firing range. In other embodiments, the detector 295 checks for blinking to make sure the drug is not dispensed during a blink but shortly upon opening of the eyelids. In some embodiments, the applicator 15 dispenses fluid 345 after a predetermined period of time after a blink event has been detected or upon opening of the eyelids at the tail end of the blink detection event.

In some embodiments and as illustrated in FIGS. 17-19, the blink detector 295 includes two reflective proximity sensors 350 and 355 in a paired arrangement to verify proper eye targeting and to detect eye blinks. In some embodiments, sensors 350 and 355 are positioned on either side of the nozzle 37. In some embodiments, each sensor 355 and 350 includes both a LED and photodiode (illustrated as 355*a* and 355*b* in FIG. 19). In some embodiments, the two sensors 350 and 355 are optical proximity infrared sensors that are configured to detect the presence of the eye 125 and determine if a blink has occurred. In some embodiments, the sensors 350 and 355 are reflective proximity sensors with lensed light collection and surface mount technology packaging. In some embodiments, the sensors 350 and 355 are OPB733TR sensors from TT Electronics of Carrollton, Tex., United States of America or HSDL-9100 sensors from Avago Technologies of San Jose, Calif., United States of America, but the sensors 350 and 355 may be any LED and photodiode detector. In some embodiments, the sensors 350 and 355 have a molded package surface above the top surfaces of their micro lenses so as to provide a convenient surface onto which a micro prism of approximately 30 degrees angle can be mounted. Generally, the sensors 350 and 355 register a balanced threshold signal indicating alignment to the eye 125 and a distance that is within a target range to the eye 125. In some embodiments, the target range to the eye (illustrated as L in FIG. 18) is about 10 mm to about 30 mm. In some embodiments, L is between about 15 mm and 20 mm.

Reflections from the eye 125 can be detected in the 15-25 mm range but predicted spatial orientation and alignment is often inaccurate when based on information from only one photo proximity pair (i.e., LED and photodiode combination). As such, the positioning of the two sensors 350 and 355 at an equal distance from the nozzle 37 results in off-axis reflected signals that can be compared. Typically, users can horizontally orient a device very accurately and can align the horizontal position accurately but suffer from poor judgement in terms of vertical angular and vertical spatial targeting. Moreover, the eye 125 typically has only 8-9 mm of clearance between the eyelids, but 18 mm of clearance over the horizontal sclera of the eye 125. As such, the clearance over the horizontal sclera is much greater than the clearance 140 between the eyelids. In addition, because of the natural curvature of the eye (typically a radius of 11.5-12.5 mm), it is difficult to direct most of the light normal to the eye 125 to optimize reflected signal intensity without mounting SMD photo proximity sensors on an angled substrate, which would result in increased cost. As such, the blink detector 295 may also include micro prisms 360 and 365 that direct the light closer to normal to the scleral and corneal surface of the eye 125, and increase the reflection signal when the eye 125 is in the optimal distance and position normal to their path. Thus, the sensors 350 and 355 and the micro prisms 360 and 365 can be used as an electronic means to detect optimal alignment of the nozzle 37 to the eyeball as well as blink detection.

When the nozzle 37 includes a plurality of openings, for example 8-10 openings roughly 300 μm in diameter and adequately spaced apart to allow for nozzle cone angle and low hydraulic losses, the dimension 120*a* of the array 120 is approximately 14 mm. As such and in some embodiments, the sensors 350 and 355 and respective micro prisms 360 and 365 are separated by about 16 mm. However, the spacing of the sensors 350 and 355 may be based on the size of the cartridge 15 and nozzle 37 and may be slightly closer together for a slit nozzle. In some embodiments, the arrangement allows an optimal micro prism angle α (illustrated in FIG. 18) for a glass (n=1.5) that maximizes the scattering of the reflected light back into the photodiode detectors of the sensors 350 and 355. In some embodiments, the micro prisms 360 and 365 are omitted.

In the vertical direction, as long as the divergence of the rays of the LED are in the range of +/−20 degrees, which is very typical, an adequate signal will be obtained, as illustrated in FIG. 19.

In some embodiments, the sensors 350 and 355 are 940 nm optical proximity sensors with detector coatings to reject sunlight outside of a +/−10 nm range. In some embodiments, natural sunlight overwhelms the amplifier signal when the impinging infrared background radiation in the wavelength range is less than 930 nm and greater than 950 nm. At 940 nm, natural sunlight has atmospheric absorption and a deep transmission dip such that very little radiation is present centered at this wavelength at the surface of the earth. As such, in some embodiments the sensors 350 and 355 are configured to have an LED that emits radiation at 940 nm and only detect wavelengths of 940 nm+/−10 nm or even more narrowly 940 nm+/−5 nm. This prevents DC detector saturation from natural sunlight. Other smaller background sources of lighting can easily be compensated for by pulsing the proximity sensors at an AC frequency and filtering out the remaining DC background.

In some embodiments, a photocurrent signal can be dropped across a detection resistor in the kΩ range and the voltage thus obtained can be buffered and low pass filter with a lower bounds threshold signal in both the left and right proximity sensors 350 and 355 to ensure the ophthalmic delivery device is well situated near the eye 125. In addition, a threshold matching signal error value between the photodiodes can be chosen to ensure the horizontal positioning or rotational angle of the device is level with the eye 125. Blink detection can be achieved by sampling and picking off a sharp transient signal that is typically higher in amplitude due to increased back scattering into the detector.

In some embodiments, alignment of the nozzle 37 with the eye 125 involves a combination of dimensional (i.e., along x, y, and z axes) alignment and angular position of the nozzle relative to the eye 125. As the surface of the eye 125 is curved, there are multiple combinations of dimensional alignment and angular position that result in the nozzle, or a longitudinal axis of the one or more openings, being aligned with the eye 125. Generally, there are three angles of rotation in pointing the nozzle 37 towards the eye 125. The first angle of rotation is in the "right" and "left" directions between nose and ear. Because the exposed part of the eye is much wider in this direction than it is tall (i.e., between eyelids), the rotational axis of the applicator sweeping along the left right direction towards the eye is not critical. The second angle of rotation is in the "top" and "bottom" directions or vertical direction between eyelids. The applicator being rotated along this angle of rotation is much more critical considering there is less exposure of the eye in this direction, and the proximity sensors 350 and 355 looks for a rotation that gives the best signal in between the two eyelids along this direction. The third angle of rotation is in a "clockwise" or "counterclockwise" direction of the nozzle relative to the eye. Again, the proximity sensors 350 and 355 look for a rotation that gives the best signal in this angle of rotation as well. Alignment of the nozzle 37 is indicated by the two proximity sensors 350 and 355 having substantially equal signals; otherwise one signal will likely be a partial reflection off part of an eyelid and one will not. Therefore, for the photodetector signals to indicate alignment, they must be a designated narrow amplitude range indicative of hitting the eyeball sclera as well as substantially equal in amplitude. In some embodiments, alignment of the nozzle 37 involves a longitudinal axis of the one of more openings being aligned with a surface of the eye such that an ejection of a fluid from the opening is aimed toward the surface of the eye 125.

In an example embodiment, the nozzle 37 is aligned directly with a light source, such as an LED (e.g., aligned without parallax), which permits the user to see the light from the light source only when the nozzle 37 is correctly aligned toward the eye 125 within a range of positions and orientations. The applicator 15 may not require gravity to function, and thus may function regardless of orientation. The applicator 15 may also include passive features intended to rest against a user's forehead or cheekbone to aid in proper alignment of the device. In one aspect, and when portions of the head 35 are transparent, a single or multicolor LED can be placed directly behind the nozzle 37 of the applicator 15 to allow for direct aiming of the nozzle 37 into the eye. With appropriate aperturing of the light rays, these rays can be confined to a small angular range that can directly pass through the one or more openings (e.g., 85, 160, 170, or 180) such that the light rays from the light source are only visible when correctly aligned with the eye 125. A user will then only see the colored LED light with high visual acuity over their eye's fovea color receptive region within a narrow aiming range such as +/−10 degrees, which assists the user in correctly aiming the device towards the eye 125, assuming the LED brightness is appropriately chosen.

If the applicator 15 distance is too far (e.g., more than 20 mm from the eye), the light source may be controlled to change in color or in illumination pattern (e.g., blinking, strobing, pulsing, solid) for example. Further, if the applicator 15 is close enough to be in range it can be changed from a first color to a second color. For example, blue and orange may be a common colorblind-friendly palette. However, any suitable color and color combination can be used. An RGB LED can be used, which is capable of a wide color gamut by adjusting relative currents to each LED. The intensity of the LED can also optionally be flickered or strobed to be used in a similar manner to a blink-defeating signal in a flash camera. Thus, through color changing and time domain changing signals, range, alignment, and aiming can be communicated to the user while they are holding the device, greatly improving the ease of use of the device.

Figure 20:
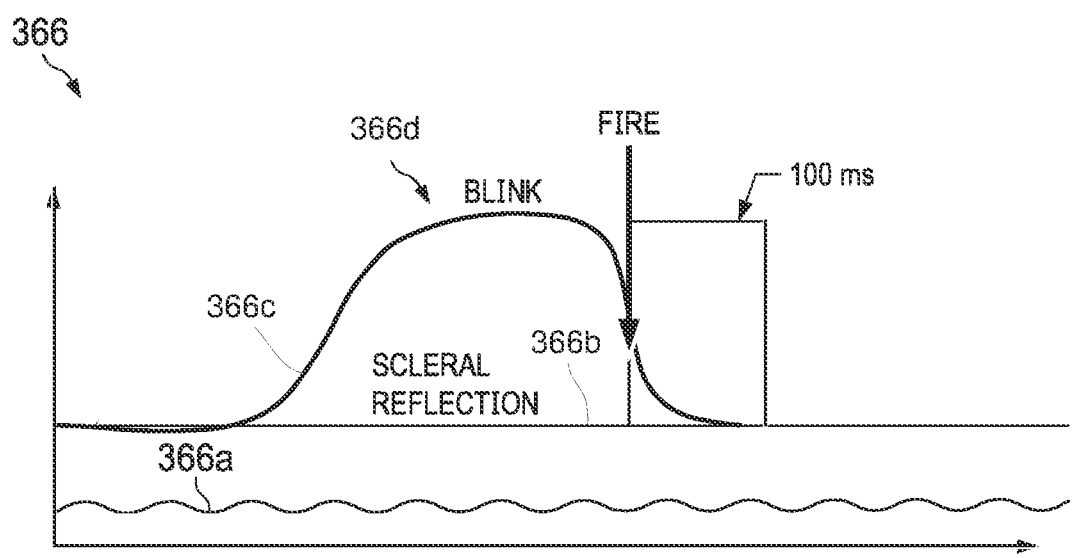
FIG. 20 is a graphical illustration of timelines of a blink detection signal that show overlapping signal traces for comparison that represent different conditions including baseline noise far away from the eye, a higher-level signal near the eye, and a transient spiked signal representing a blink event in accordance with at least one embodiment of the present disclosure.

In some embodiments, the blink detector 295 includes or is in communication with the controller 290 that instructs the trigger 305 to activate or to dispense a dose. In some embodiments, the controller 290 determines whether the applicator 15 is being manually armed (e.g., is the user pressing the mechanical activation button 320) by checking an "ON" signal. In some embodiment, the controller 290 also determines whether the low pass filtered optical reflective sensor targeting signals for the sensors 350 and 355 are above threshold voltage for both their average values and below threshold for their difference values. In some embodiments, the controller 290 has at least 2 separate 8 bit ADC channels and the low pass filter is easiest to implement in software after the raw data has been captured by the analog to digital converters. In some embodiment, the controller 290 also determines whether the unfiltered higher bandwidth blink signals should trigger an ON signal on a quick rising or falling edge transition of the proximity sensors signifying that a blink is beginning or ending. The details of whether the rising or falling edge of the proximity sensor signal signifies a blink opening or closing depend upon the alignment of the central ray of the proximity sensor LEDs. FIG. 20 illustrates a timeline designated by the numeral 366 during which the controller 290 determines that a blink has occurred and causes the trigger 305 to dispense a dose. Generally, the light from the blink detector LEDs is pulsed at a frequency between 100 Hz and 10 kHz which is much faster than a blink transient at the 10 Hz level. The DC component of the corresponding optical sensors is filtered out. The remaining AC component is amplified and filtered into a smooth function over time. Generally, there is a baseline transimpedance amplified noisy signal from the proximity sensor when it is far away from the eye, which is indicated by a ripple signal due to background lighting and noise. Once the applicator 15 is brought within aiming distance to the eye 125, a higher value base signal detected. When the user blinks, the higher value base signal spikes. FIG. 20 illustrates a line 366*a* that represents an expected ripple signal that is associated with the sensors not being aligned with the eye; a line 366*b* that represents an expected higher value base signal that is associated with the sensors being aligned with the eye; and a line 366*c* represents an actual signal over time as the sensors are aligned with the eye (e.g., when the line 366*c* is close to the line 366*b*) and then a transient spike 366*d* of the line 366*c* that is associated with the user closing and then opening the eyelids. As illustrated, the line 366*c* returns to the baseline 366*b* after the user re-opens his or her eyelids. Generally, when the higher value base signal is balanced between both proximity sensors, then as the user blinks two blink signals will be recorded as the transient spike upon closing and opening the eyelids. In general, when the eyelids are closed the signal is stronger as long as the primary central axis LED ray hits the eyeball slightly off-axis. The details of how these signals are shaped and their detailed amplitude and time domain characteristics vary slightly from one person to the next based on eyelashes, skin color, and blink duration, and machine learning can be used to pinpoint the characteristic transient signals of each individual user and store this data in memory to help perfect the blink detection algorithms.

Figure 21:
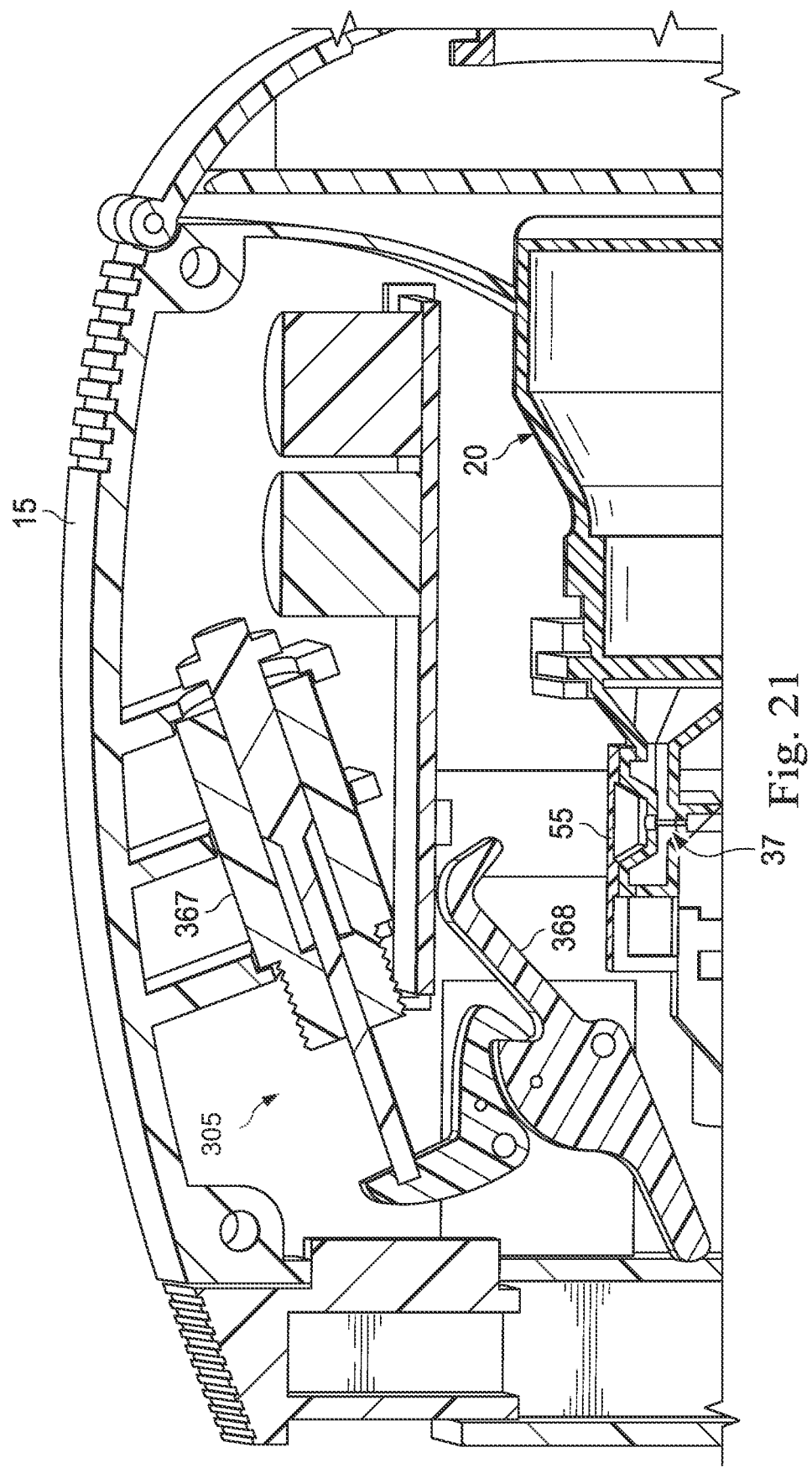
FIG. 21 is a cross-sectional view of a portion of the device of FIG. 1, in accordance with at least one embodiment of the present disclosure.

In some embodiments, the trigger 305 is or includes an electromechanical solenoid that strikes the elastomeric wall 55. In other embodiments and as illustrated in FIG. 21, the trigger 305 is or includes an electromechanical solenoid 367 that is coupled to an arm or latch trigger 368 that strikes the wall 55. Generally, the trigger 305 is activated by an electrical signal and causes a hard tip object (e.g., portion of solenoid or latch trigger 368) to strike the wall 55 and creates an instantaneous impulse of momentum that imparts a pressure shock wave that builds up pressure suddenly in the holding chamber 62 and imparts positive displacement of the fluid through the nozzle 37. The holding chamber 62 accommodates fluid prior to ejection. The impact can come from any type of mechanical mechanism that builds up mechanical energy including, such as for example a leaf spring with a pullback mechanism, a torsional spring with windup mechanism, or a hammer with a cocking and trigger mechanical mechanism. In some embodiments, the trigger 305 includes a direct solenoid that is of the bi-stable type using springs and/or magnets that can have a holding force large enough to maintain the wall 55 in a displaced state in which the wall 55 covers the opening(s) of the nozzle 37. Generally, the wall 55 can be displaced by any mechanical mechanism with sufficient impact force. Building up too low a momentum during the strike of the wall 55 can result in viscous drool out of the nozzle 37 as the wall 55 stops too slowly upon covering or contacting the interior surface of the nozzle 37. In some embodiments, the velocity of the fluid out of the nozzle 37 is between 1.5 m/s and 3 m/s. However, in some embodiments, the velocity at which the fluid is ejected is between about 1.5 m/s to about 2 m/s. Moreover, with a volume of liquid delivered of 10-15 µl, the stream must be fast enough to defeat the blink reflex at approximately less than 100 ms. However, by triggering off the opening of an eye blink, extra time is afforded as it takes longer to turn a blink around from an opening state to re-closing of the eyelids. In general, the total time to deliver liquid to the eye is well under 100 ms, as the blink detection circuit takes under 40 ms, the solenoid actuation takes under 10 ms, the movement of the wall takes under 5 ms, and the ejection of fluid takes under 20 ms. Another issue with too low a strike impact can result in too low a velocity below 1.5 m/s resulting in loss of aiming from a gravitational parabolic trajectory. Too high a velocity, however, can result in a noticeable unpleasant impact on the eye 125. Because of the high mass of the striker, it is not necessary that the strike velocity be the same as the microstream ejected from the nozzles. In some embodiments, to achieve a "sheet" microstream having a velocity of between 1.5-3 m/s, the average velocity of the portion of the trigger 305 striking the wall 55 is at least 0.5 m/s and up to 3 m/s at the moment of impact and a momentum mass coming from a hammer or a direct solenoid armature if made from metal is between 2 grams and 3 grams. In order for the wall 55 to shut off the nozzle 37 and maintain its positive displacement after the strike, there is an additional holding force typically between 0.5 N-2N required for maintaining the wall 55 in the full displaced state. However, the exact force depends upon the exact elastic mechanical properties and geometry of the elastomer wall.

In some embodiments, the nozzle cap 50 is opened prior to the ejection of the fluid by a mechanical linkage to the activation button 320 when the cartridge 20 is inserted in the applicator 15. Because the cap 50 is an integral part of the head 35 in some embodiments, it does not need to maintain mechanical integrity for years but only as long as the cartridge 20 itself is used, typically 1-2 months and thus the cap 50 is disposed of with the cartridge 20. In a typical eye dropper device bottle, a user manually releases squeeze pressure and non-sterile air re-enters through the same nozzle. With this device 10, the nozzle 37 can be recapped via the cap 50 before the wall 55 is released and the holding chamber 62 draws in new fluid. This simultaneously allows for sterile filtered air to be taken in through a separate sterile air intake filter (e.g., air entry port 45) to achieve equal pressurization.

Figure 22:
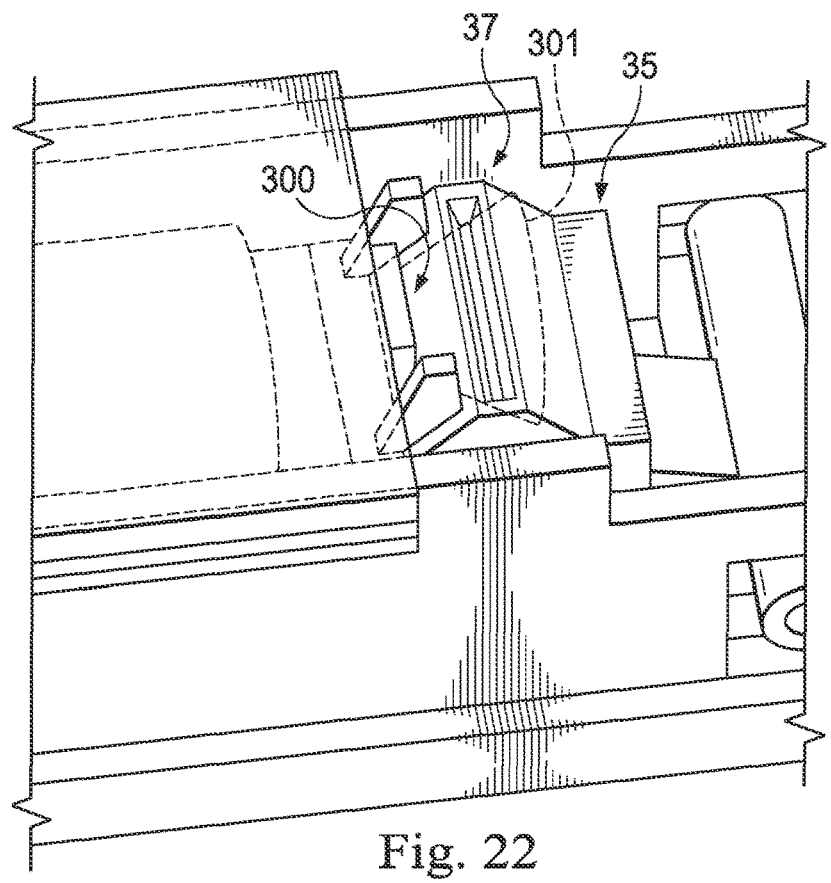
FIG. 22 is a perspective cutaway view of the cartridge and the applicator of FIG. 1, in accordance with at least one embodiment of the present disclosure.
Figure 23:
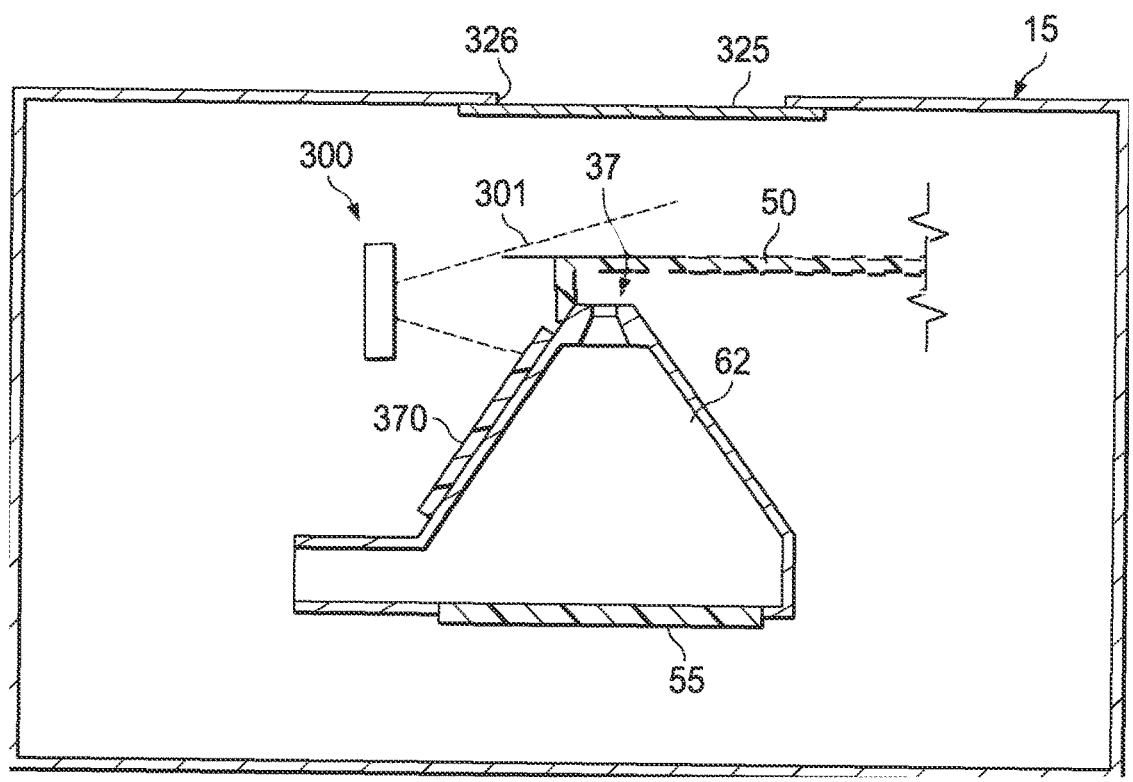
FIG. 23 is a diagrammatic illustration of the applicator and the cartridge of FIG. 1, in accordance with at least one embodiment of the present disclosure.

In some embodiments and as illustrated in FIGS. 22 and 23, there is an additional sterilizer 300 that consists of one or two ultraviolet ("UV") light emitting diodes ("LEDs") that are positioned relative to the nozzle 37 such that the nozzle 37 is exposed to an LED light cone 301 through either the tip of the nozzle head or the cap 50. In addition, and in some embodiments, because constant power to the UV LED uses a substantial amount of battery energy, the UV LED can be turned on just after an application to the eye and after the dust cover 325 is re-closed for protection. Due to the close proximity of the UV LED to the nozzle 37, only a few seconds of exposure is necessary for sterility using the appropriate wavelength. At the appropriate UVC wavelength range of 285 nm for example, the UV LED is known to kill viruses, bacteria, and even molds very effectively with over 10^3 reductions with only millijoules of energy over a concentrated close proximity area. The use of the UV LED is an extra precaution that means any residue remaining at the tip is re-sterilized. In the embodiments in which the cap 50 extends between the nozzle 37 and the sterilizer 300, for example as illustrated in FIG. 23, the cap 50 and/or material forming the moisture chamber 515 is at least partially transparent to the UV wavelength and is made from UV stabilized materials.

In some embodiments, a UV shield 370 is applied over a portion of the nozzle 37 or other portion of the head 35. For example, the UV shield 370 may include a thin layer of sputtered SiO2 or metal to prevent a portion of the nozzle 37 from exposure to the UV light. In some embodiments, the UV shield 370 prevents the potential for degradation of a drug component of the viscous fluid in the main holding chamber 62 and only affects a small concentrated area around the nozzle.

As illustrated in FIG. 22, an example sterilizer 300 that includes a SMD UV LED is coupled to the applicator 15 and situated near the nozzle 37. An example of a SMD UV LED includes for example the L944-UV265-4 265 nm domed UVC LED from American Opto Plus LED. In addition to UV-C LEDs killing bacteria, UV-C LEDs also kill mold spores. While described as a sterilizer 300, the sterilizer 300 is not required to kill all of the bacteria, viruses, and fungi. Instead, the sterilizer 300 may kill or reduce a significant portion of the bacteria, viruses, and fungi by several orders of magnitude. In some cases, this may result in ocular drug formulations which can be completely preservative free, which is highly desirable. In other cases, the use of preservatives may be dramatically reduced. It should be noted that under operations, the nozzle cover 50 is not touched or removed by the user from the cartridge in any way but is permanently tethered to it at some point, and is held back further from the eyelashes than a normal eye dropper. Generally, the dust cover 325 of the applicator 15 also keeps the nozzle cover or cap 50 clean and prevents UV from leaking outside the applicator when the sterilizer 300 is turned on. The only chance for biological contamination is an airborne event during liquid dispensing. However, the diffusion time and diffusion rates for even the fastest self-propelled bacteria is slow enough so as to be killed by the UV light near the nozzle 37 before any growth can take place. Additionally, the nozzle 37 is covered internally by the elastomeric wall 55 after dispensing events, which acts as a valve trapping any such biological contamination. In some embodiments, the wall 55 can remain against the nozzle 37 until after a brief UV exposure has taken place.

In some embodiments, the power source 285 is a rechargeable battery, such as a small coin cell of LiPo battery.

In some embodiments, the transmitter 280 of the applicator 15 is in communication with the transmitter 265 of the cradle 255. Communication between the transmitters 280 and 265 and/or between the transmitters 280 and 265 and the remote device 250 allow for tracking the use of the device 10. In some embodiments, communication and connectivity between the cradle 255, the applicator 15, and/or the remote device 250 allows for time and date tracking of medications, syncing between different devices that are similar or identical to the device 10, auto-re-ordering of medications, providing battery recharge reminders, providing reminders to the user to take medication, enables doctor/patient sharing, improving telemedicine options, and/or tracks treatment compliance. Communication and connectivity between the cradle 255, the applicator 15, and/or the remote device 250 allows for the applicator 15 to be trained based on historical data. Some examples of training the applicator 15 include updating algorithms and/or calculations using data regarding scleral baseline proximity reflection, skin reflection, movement off axis and centering signals, and blink temporal dynamics.

Figure 24:
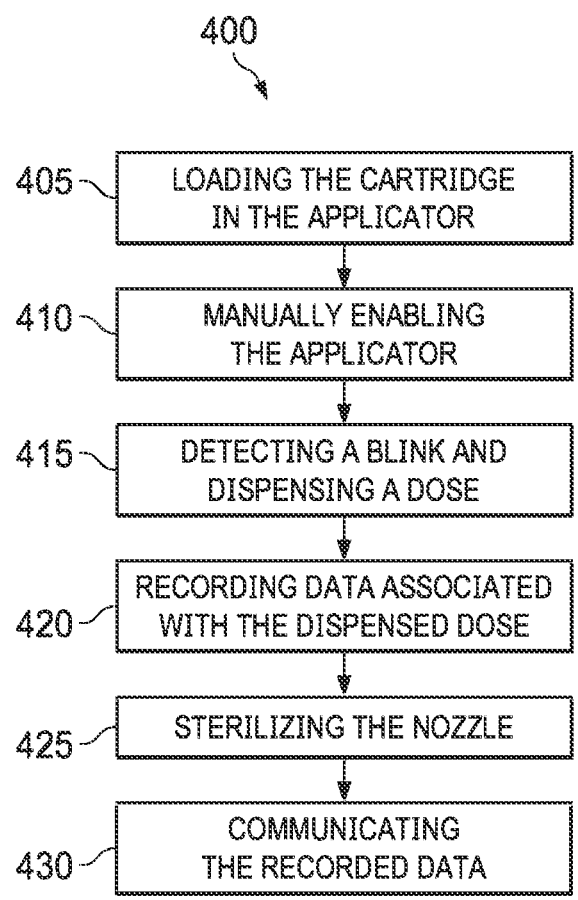
FIG. 24 is a flow chart illustration of a method of operating the device of FIG. 1, according to an example embodiment.

In an example embodiment, as illustrated in FIG. 24 with continuing reference to FIGS. 1-23, a method 400 of operating the device 10 includes loading the cartridge 20 in the applicator 15 at step 405; manually enabling the applicator 15 and opening the dust cover 325 at step 410; detecting a blink and dispensing a dose at step 415; recording data associated with the dispensed dose at step 420; sterilizing the nozzle 37 at step 425; and communicating the recorded data via the transmitters 265 and 280 at step 430.

Figure 25A:
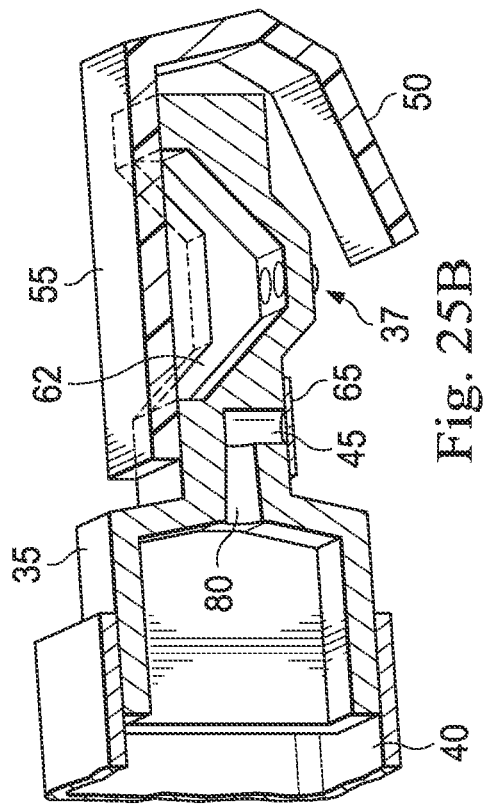
FIG. 25A is a perspective cutaway view of the cartridge of FIG. 1 during a step of the method of FIG. 24, in accordance with an embodiment of the present disclosure.

At step 405 and in one embodiment, the cartridge 20 is loaded in the applicator 15. In some embodiments, the cartridge 20 is disposable. Generally, when the cartridge 20 is accommodated in the applicator 15 but the applicator 15 is not loaded, the head 35 is in a first configuration as illustrated in FIG. 25A. As illustrated, the cap 50 is positioned against the nozzle 37 and the wall 55 is not depressed. Fluid is accommodated in the holding chamber 62.

Figure 25B:
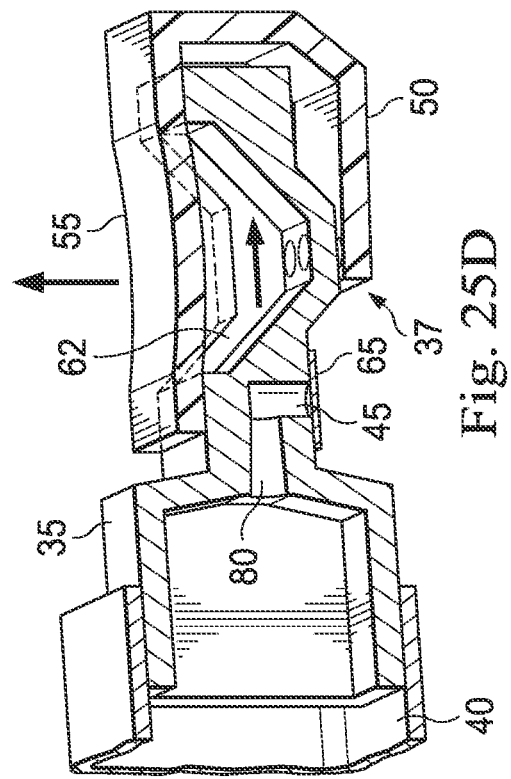
FIG. 25B is a perspective cutaway view of the cartridge of FIG. 1 during another step of the method of FIG. 24, in accordance with an embodiment of the present disclosure.

At the step 410 and in one embodiment, the applicator 15 is activated with mechanically or electrically loaded energy preparing for a strike to wall 55. One example of the applicator 15 being manually enabled is when the user depresses the activation and the mechanical activation button 320. The head 35 transitions from the first configuration to a second configuration in which the cap 50 is spaced from the nozzle 37 such that the fluid exiting the nozzle 37 will clear the cap 50, as illustrated in FIG. 25B. In some embodiments, the applicator 15 is enabled when the user depresses mechanical activation button 320 but is not fired until the blink detector 295 determines that the applicator 15 is correctly positioned relative to the eye 125 of the user and in response to a detected blink.

Figure 25C:
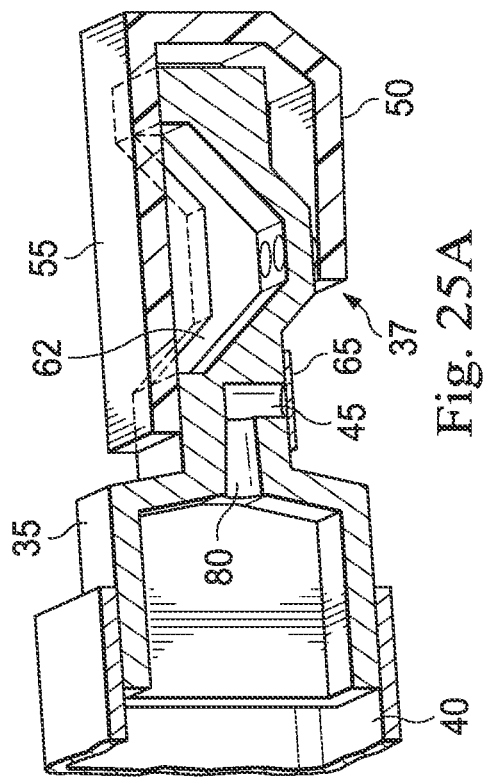
FIG. 25C is a perspective cutaway view of the cartridge of FIG. 1 during another step of the method of FIG. 24, in accordance with an embodiment of the present disclosure.
Figure 25D:
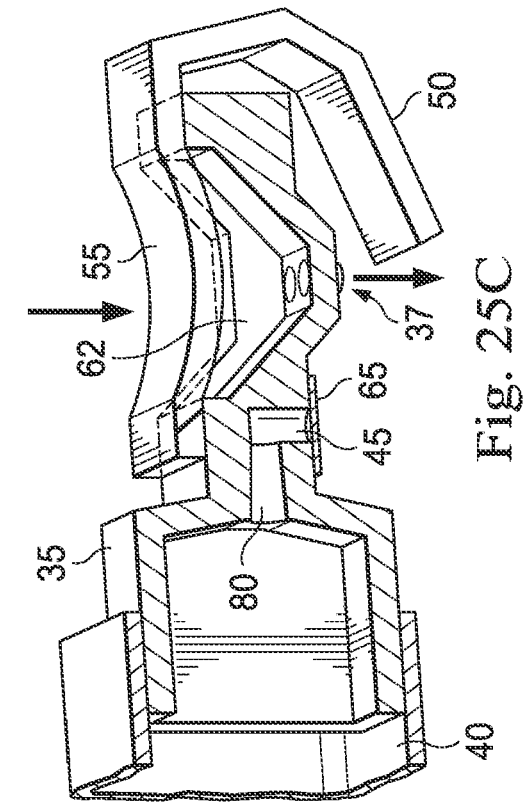
FIG. 25D is a perspective cutaway view of the cartridge of FIG. 1 during another step of the method of FIG. 24, in accordance with an embodiment of the present disclosure.

At the step 415 and in one embodiment, a blink is detected and a dose is dispensed. As detailed above and illustrated in FIG. 19, the blink detector 295 determines that the nozzle 37 is aligned with the eye 125 and detects a blink. Upon detecting a blink, the controller 290 sends a signal to the trigger 305 to dispense the dose. The head 35 also transitions from the second configuration to the third configuration in which the wall 55 is depressed to force the fluid from the holding chamber 62 via the nozzle 37, as illustrated in FIG. 25C. The external impact to the wall 55 should be sudden and much faster than the eye blink reflex time of approximately 100 ms. In one embodiment, the impact duration is on the order of 10 ms or faster. Generally, the wall 55 is made from a soft enough elastomeric material that the wall 55 highly dampens out any rebounds from this strike impact and also soft enough that the inertia resisting the impact of this strike can be largely attributed near the end of motion to the squeeze-film damping of the fluid itself. In some embodiments, the wall 55 is hit with an instantaneous impulse of momentum already in motion which imparts a pressure shock wave that builds up pressure suddenly. After dispensing, the head 35 also transitions from the third configuration to the fourth configuration in which first the cap 50 extends over the nozzle 37 and then the wall 55 is released from its depressed state and the, which prevents air from being drawn in through the nozzle 37 and instead draws fluid from the chamber 40 into the holding chamber 62, as illustrated in FIG. 25D.

At the step 420 and in some embodiments, the controller 290 records data associated with the dispensed dose. In some embodiments, the controller records data detected by the blink detector 295 and data detected or generated by the trigger 305. As such, the controller 290 detects the timing of each dose being dispensed. Moreover, the controller 290 can detect and record a blink speed of the user.

At the step 425 and in some embodiments, after the dust cover 325 is reclosed, the sterilizer 300 sterilizes the nozzle 37 at step 425. In some embodiments and in response to a detected dose being dispensed by the controller 290, the controller 290 activates the sterilizer 300 for a predetermined period of time to sterilize a portion of the nozzle 37 and/or fluid passing via the nozzle 37.

At the step 430 and in some embodiments, the recorded data is communicated via the transmitters 265 and 280. In some embodiments, the recorded data is transmitted to the transmitter 265 and/or the remote device 250. In some embodiments, data is transmitted from the transmitter 265 to the transmitter 280. In some embodiments, the recorded data is stored in the controller 275. However, the recorded data is also stored or received by the remote device 250 via the network 260. The controller 290 may upload and update the recorded data, which may span months to years, to a cloud-based database via the controller 275. This recorded data can be used to update, customize, and generate predictive models to refine dry eye management over the course of hours to days. The models may include a variety of factors including historical, current, and expected or predicted external factors, which are used to generate predictive models.

Figure 26:
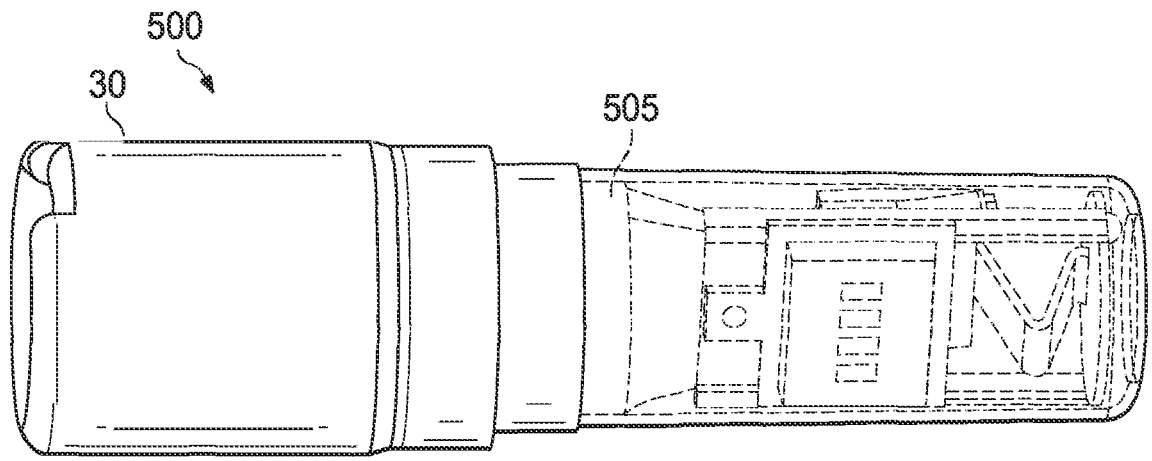
FIG. 26 is a perspective view of the cartridge of FIG. 1, in accordance with yet another embodiment of the present disclosure.
Figure 27:
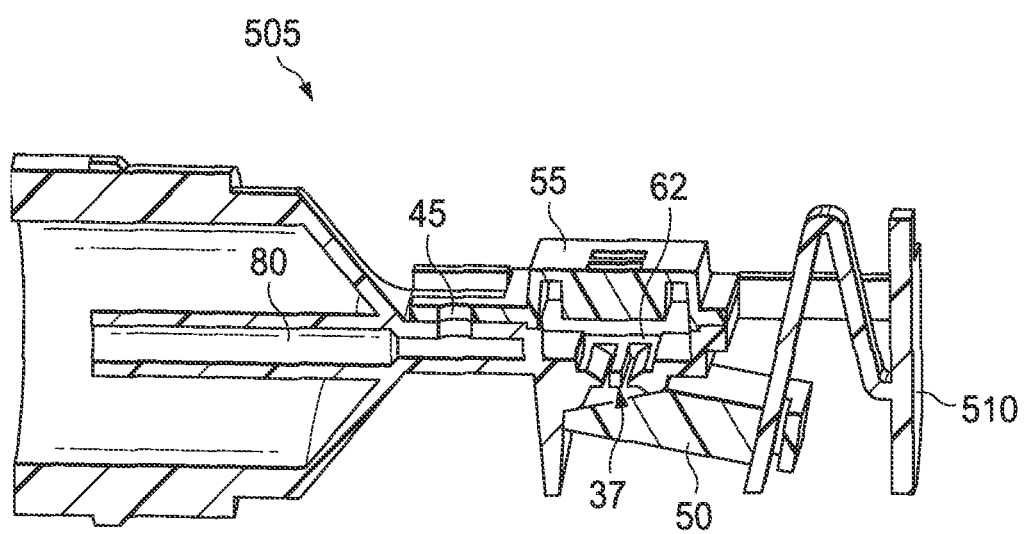
FIG. 27 is a perspective cutaway view of the cartridge of FIG. 26, in accordance with another embodiment of the present disclosure.
Figure 28:
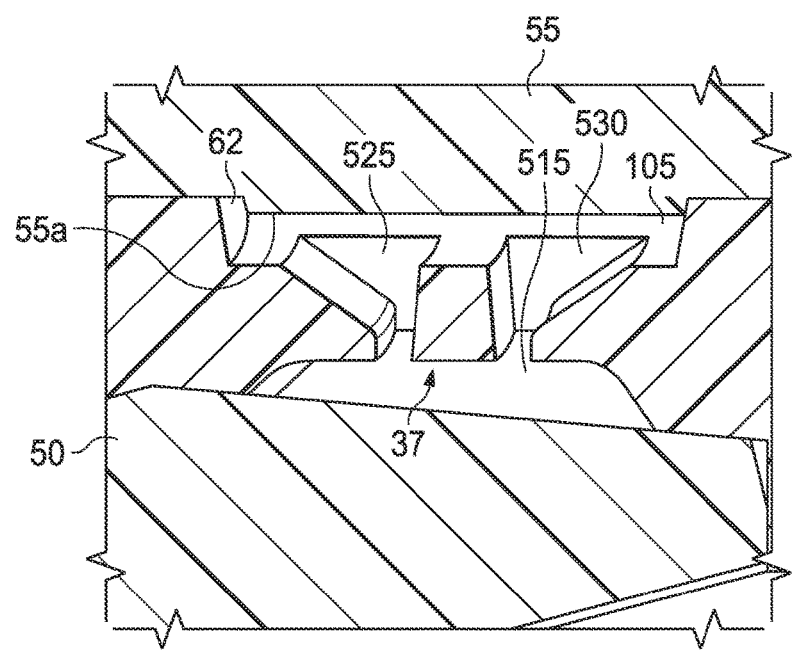
FIG. 28 is a cross-sectional view of a portion of the cartridge of FIG. 26, in accordance with another embodiment of the present disclosure.

FIG. 26 illustrates another embodiment of the cartridge 20 designated with the reference numeral 500. In some embodiments, and instead of a rectangular shaped body, the housing 30 is cylindrical shaped. Moreover, the cartridge 500 includes a head 505, that may optionally include a cylindrical protective head cover the user removes before loading the cartridge 500 into the applicator that is another embodiment of the head 35. As illustrated in FIGS. 26 and 27, the head 505 is similar to the head 35 in that it includes the wall 55 and the nozzle 37 that form the holding chamber 62. In this embodiment, the air vent 45 is positioned on a top side of the head 505 (e.g., a side that includes the wall 55) instead of a bottom side (e.g., a side that includes the nozzle 37). In some embodiments, the cap 50 of the head 505 is not integrally formed with the wall 55 and is instead coupled to a spring 510 or other energy-storage device that forms a portion of the head 505. As discussed previously, the cap 50 stays in a closed position unless fluid is about to be or is being ejected from the nozzle 37 at which time the cap 50 transitions into an open position. In some embodiments and as illustrated in FIG. 26-28, the cap 50 is spaced from the nozzle 37 when in the closed position to form a moisture chamber 515 between the nozzle 37 and the cap 50. In some embodiments, spacing of the cap 50 from the nozzle 37 when in the closed position reduces the likelihood of contaminating the nozzle 37 with the cap 50 as the nozzle is never directly touched. FIG. 28 is a close up cutaway is one that contains two slots like the oblong openings also depicted in FIG. 27.

Figure 29:
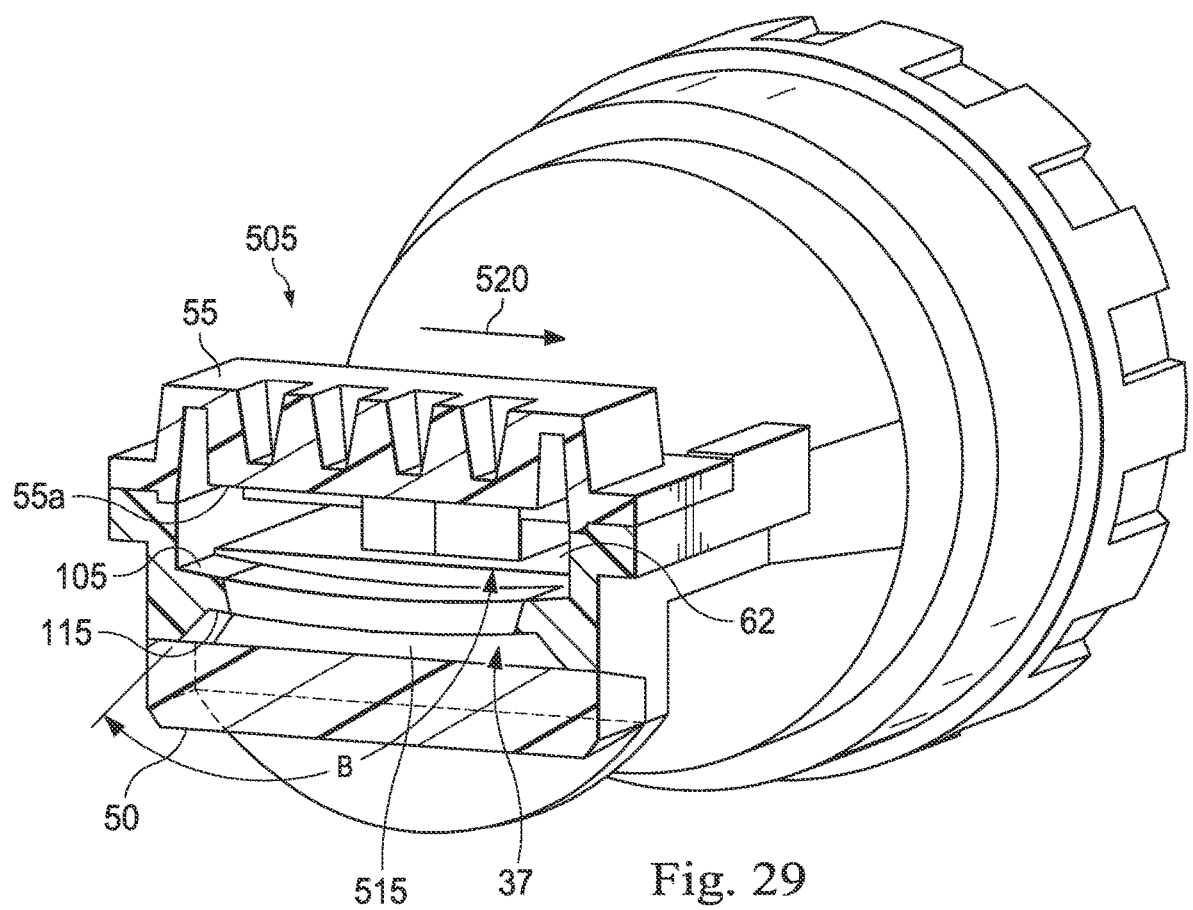
FIG. 29 is another perspective cutaway view of the cartridge of FIG. 26, in accordance with another embodiment of the present disclosure.

In some embodiments and as illustrated in FIG. 29, the nozzle 37 forms a single opening or more than one opening that extends along a direction 520 and the internal surface 105 forms a concave-like or curved surface and the external surface 115 forms a convex-like or curved surface. The surfaces 105 and 115 being curved encourages the fluid exiting the nozzle 37 to form a more fan-like shape after exiting. That is, fluid exiting opposing edges of the nozzle 37 exit at an angle B that is not perpendicular to the direction 520. In some embodiments, the surfaces 105 and 115 being curved encourages the resulting drop footprint to be more highly elliptical or an eccentric stadium shape rather than more rounded in profile or oval shaped for larger travel distances to the eye.

In some embodiments, the wall 55 has an interior surface 55a that forms a portion of the holding chamber 62 and that contacts the interior surface 105 during the ejection of the fluid. In this embodiment, when a force is applied on the wall 55, the wall 55 deforms towards the nozzle 37 thereby reducing the volume of the holding chamber 62 and forcing the fluid from the nozzle 37. Moreover, the wall 55 deforms until the interior surface 55a contacts the nozzle 37 inner face, or interior surface 105, thereby sealing or otherwise temporarily blocking the openings. As such, movement of the wall 55 toward the nozzle 37 not only disperses the fluid but closes the openings of the nozzle 37 to end the ejection of the fluid. As such and in some embodiments, the wall 55 forms a valve that closes the nozzle 37. Movement of the wall 55 to its natural state (after being struck) fills the holding chamber 62 with fluid from the chamber 40 to prepare for another ejection of fluid. In some embodiments and as illustrated in FIGS. 26-29, there are two slit openings 525 and 530 that extend in parallel along the direction 520 to form an oblong shape.

Figure 30:
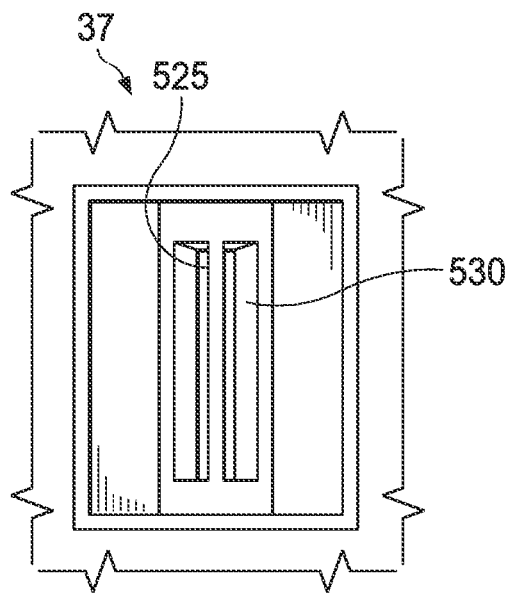
FIG. 30 is a diagrammatic illustration of the opening of the cartridge of FIG. 26, in accordance with an embodiment of the present disclosure.

In some embodiments and as illustrated in FIG. 30, a single nozzle opening is formed 535 that generally extends the direction 520 with repeating "S" shapes to form an oblong shape. This shape has larger undulations as discussed in FIG. 11 that allow for a large volume of fluid to be dispensed under the same strike energy with a single microstream tail in a confined nozzle face area.

Figure 31:
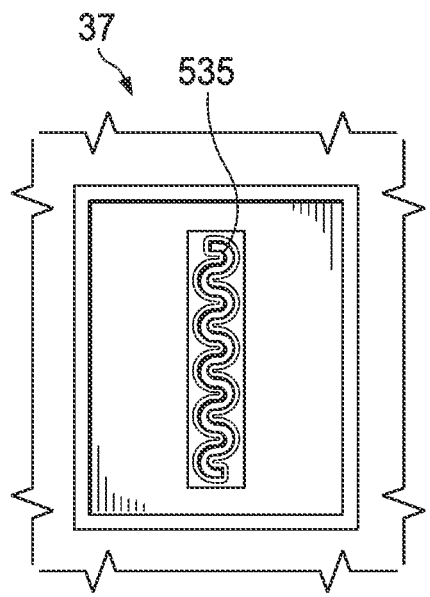
FIG. 31 is a diagrammatic illustration of the opening of the cartridge of FIG. 26, in accordance with another embodiment of the present disclosure.
Figure 32:
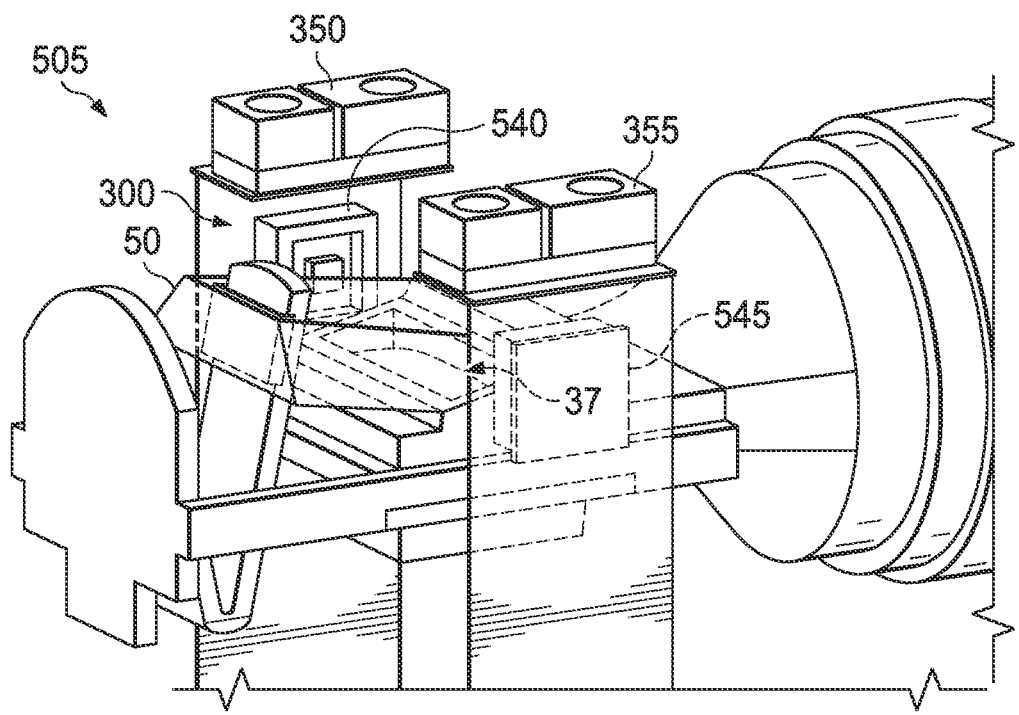
FIG. 32 is a perspective view of the cartridge of FIG. 26 and the blink detector and sterilizer of FIG. 16, in accordance with at least one embodiment of the present disclosure.
Figure 33:
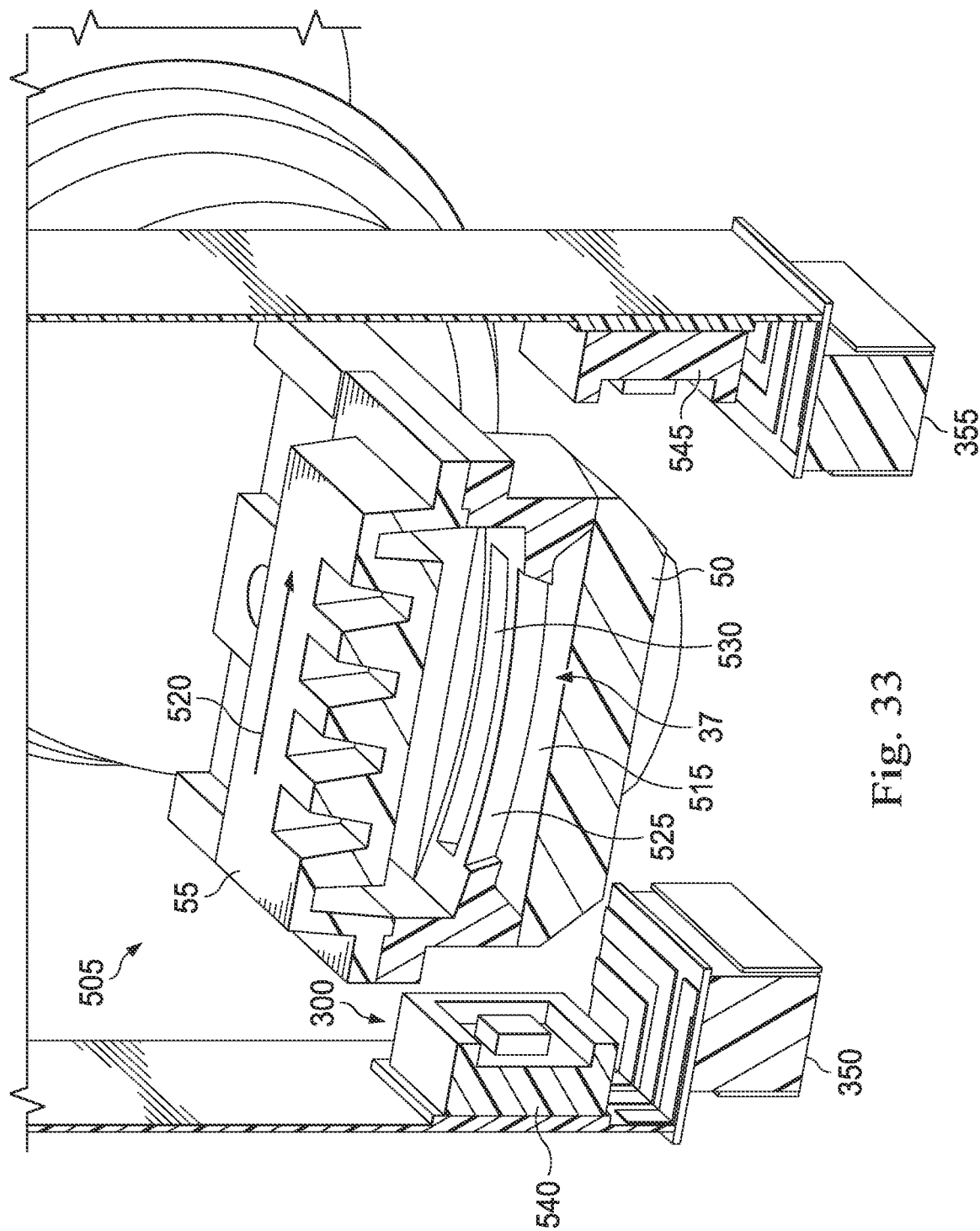
FIG. 33 is a perspective cutaway view of the cartridge of FIG. 26 and the sterilizer of FIG. 16, in accordance with at least one embodiment of the present disclosure.

In some embodiments and as illustrated in FIGS. 31-32, the sterilizer 300 includes a first and second head 540 and 545 that emit UV light from opposing sides of the head 505 towards the nozzle 37 or the nozzle moisture chamber 515. In this embodiment, the slots 525 and 530 extend between the first and second heads 540 and 545 and the light is emitted in a generally parallel direction to the direction 520.

In some embodiments, the device 10 includes a simple cartridge 20 that is placed in a smart applicator 15 that has a cradle 255 that allows for the continuous or intermittent sterilization of the nozzle 37.

In some embodiments, the nozzle 37 is a polypropylene (PP) or polyethylene (PE) plastic molded nozzle. In some embodiments, the head 35 includes polypropylene as it has favorable material properties for being directly welded to the elastomer material of the wall 55, such as with a precision high speed laser welding process. In some embodiments, the cap 50 is an over molded or welded elastomer flap. In some embodiments, the wall 55 is a heat bonded, ultrasonically bonded or laser welded to another portion of the head 35. Generally, the wall 55 facilitates easy squeezing (i.e. low displacement forces) of fluid out of the holding chamber 62 and through the nozzle 37. If the wall 55 is connected to the cap 50, it also allows easy self-contained capping of the nozzle 37 which conforms to microscopic surface roughness after a dispensing event. The wall 55 may be formed from any material that heat-welds with strength to PE or PP. In some embodiments, the wall 55 is or includes a compatible medical grade version of thermoplastic elastomers (TPEs) known as thermoplastic vulcanizates ("TPVs") with a PP cross linked polymer backbone incorporating a vulcanized rubber elastomer. In some embodiments, the TPEs may include for example medical grades of Santoprene® from ExxonMobil Chemical, Medalist® from Teknor Apex, or ProFlex™ SEBS from Foster Corporation, which have chemical and melt compatibilities with both PE and especially PP and performance characteristics such as a low amount of compression set. In some embodiments, durometer values for the material forming the wall 55 are in the range of 40-60 Shore A, making them much less rigid and more deformable than PE or PP.

The device 10 is not limited to delivery of fluids to the eye, but could also deliver fluids to the nose via a nasal spray, as higher viscosity in nasal sprays is advantageous for improving the residence time of the drug on the nasal mucosal lining.

In some embodiments, the device 10 includes a flow mechanism or general configuration to prevent uptake of unsterile air such that it maintains internal pressure and sterility over a prescribed amount of time.

In an example embodiment, the network 260 includes the Internet, one or more local area networks, one or more wide area networks, one or more cellular networks, one or more wireless networks, one or more voice networks, one or more data networks, one or more communication systems, and/or any combination thereof.

In some embodiments, a viscous fluid is a fluid having a high viscosity of 50 cps to 200 cps. While this high viscosity has been a focus of discussion, it should be noted that lower viscosities in the range of 0.5-50 cps can be used if the nozzle slit width and strike force are optimized.

Figure 34:
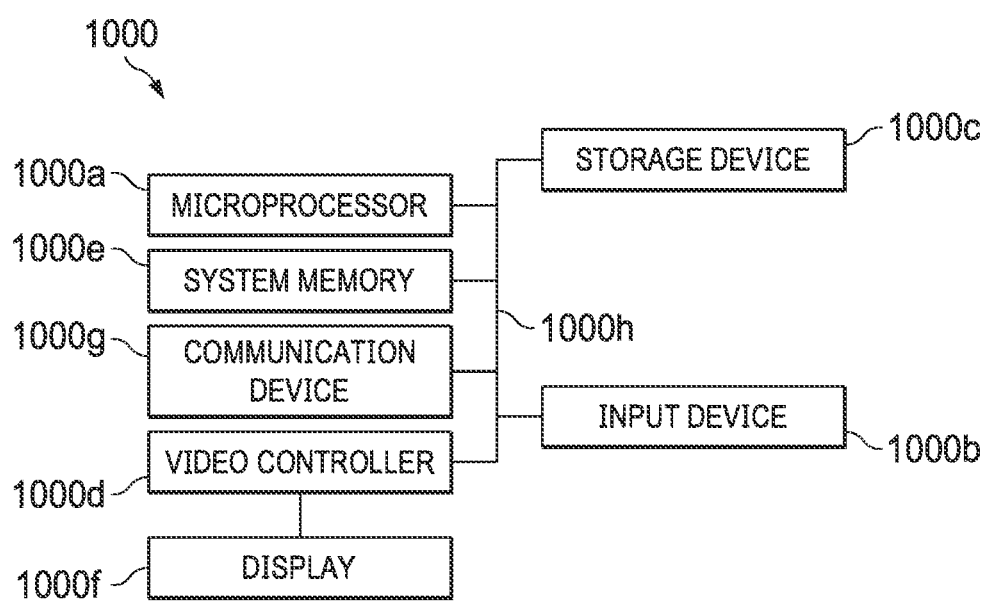
FIG. 34 is a diagrammatic illustration of a node for implementing one or more example embodiments of the present disclosure, according to an example embodiment.

In an example embodiment, as illustrated in FIG. 34 with continuing reference to FIGS. 1-23, 24A, 24B, 24C, and 24D, an illustrative node 1000 for implementing one or more of the example embodiments described above and/or illustrated in FIGS. 1-9A, 9B, 23, 24A, 24B, 24C, 24D, and 25-33 is depicted. The node 1000 includes a microprocessor 1000a, an input device 1000b, a storage device 1000c, a video controller 1000d, a system memory 1000e, a display 1000f, and a communication device 1000g all interconnected by one or more buses 1000h. In several example embodiments, the storage device 1000c may include a floppy drive, hard drive, CD-ROM, optical drive, any other form of storage device and/or any combination thereof. In several example embodiments, the storage device 1000c may include, and/or be capable of receiving, a floppy disk, CD-ROM, DVD-ROM, or any other form of computer-readable medium that may contain executable instructions. In several example embodiments, the communication device 1000g may include a modem, network card, or any other device to enable the node to communicate with other nodes. In several example embodiments, any node represents a plurality of interconnected (whether by intranet or Internet) computer systems, including without limitation, personal computers, mainframes, PDAs, smartphones, and cell phones.

In several example embodiments, one or more of the components of the systems described above and/or illustrated in FIGS. 1-9A, 9B, 23, 24A, 24B, 24C, 24D, and 25-33 include at least the node 1000 and/or components thereof, and/or one or more nodes that are substantially similar to the node 1000 and/or components thereof. In several example embodiments, one or more of the above-described components of the node 1000, the device 10, and/or the example embodiments described above and/or illustrated in FIGS. 1-9A, 9B, 23, 24A, 24B, 24C, 24D, and 25-33 include respective pluralities of same components.

In several example embodiments, one or more of the applications, systems, and application programs described above and/or illustrated in FIGS. 1-9A, 9B, 23, 24A, 24B, 24C, 24D, and 25-33 include a computer program that includes a plurality of instructions, data, and/or any combination thereof; an application written in, for example, Arena, HyperText Markup Language (HTML), Cascading Style Sheets (CSS), JavaScript, Extensible Markup Language (XML), asynchronous JavaScript and XML (Ajax), and/or any combination thereof; a web-based application written in, for example, Java or Adobe Flex, which in several example embodiments pulls real-time information from one or more servers, automatically refreshing with latest information at a predetermined time increment; or any combination thereof.

In several example embodiments, a computer system typically includes at least hardware capable of executing machine readable instructions, as well as the software for executing acts (typically machine-readable instructions) that produce a desired result. In several example embodiments, a computer system may include hybrids of hardware and software, as well as computer subsystems.

In several example embodiments, hardware generally includes at least processor-capable platforms, such as client-machines (also known as personal computers or servers), and hand-held processing devices (such as smartphones, tablet computers, personal digital assistants (PDAs), or personal computing devices (PCDs), for example). In several example embodiments, hardware may include any physical device that is capable of storing machine-readable instructions, such as memory or other data storage devices. In several example embodiments, other forms of hardware include hardware subsystems, including transfer devices such as modems, modem cards, ports, and port cards, for example.

In several example embodiments, software includes any machine code stored in any memory medium, such as RAM or ROM, and machine code stored on other devices (such as floppy disks, flash memory, or a CD ROM, for example). In several example embodiments, software may include source or object code. In several example embodiments, software encompasses any set of instructions capable of being executed on a node such as, for example, on a client machine or server.

In several example embodiments, combinations of software and hardware could also be used for providing enhanced functionality and performance for certain embodiments of the present disclosure. In an example embodiment, software functions may be directly manufactured into a silicon chip. Accordingly, it should be understood that combinations of hardware and software are also included within the definition of a computer system and are thus envisioned by the present disclosure as possible equivalent structures and equivalent methods.

In several example embodiments, computer readable mediums include, for example, passive data storage, such as a random-access memory (RAM) as well as semi-permanent data storage such as a compact disk read only memory (CD-ROM). One or more example embodiments of the present disclosure may be embodied in the RAM of a computer to transform a standard computer into a new specific computing machine. In several example embodiments, data structures are defined organizations of data that may enable an embodiment of the present disclosure. In an example embodiment, a data structure may provide an organization of data, or an organization of executable code.

In several example embodiments, any networks and/or one or more portions thereof may be designed to work on any specific architecture. In an example embodiment, one or more portions of any networks may be executed on a single computer, local area networks, client-server networks, wide area networks, internets, hand-held and other portable and wireless devices, and networks.

In several example embodiments, a database may be any standard or proprietary database software. In several example embodiments, the database may have fields, records, data, and other database elements that may be associated through database specific software. In several example embodiments, data may be mapped. In several example embodiments, mapping is the process of associating one data entry with another data entry. In an example embodiment, the data contained in the location of a character file can be mapped to a field in a second table. In several example embodiments, the physical location of the database is not limiting, and the database may be distributed. In an example embodiment, the database may exist remotely from the server, and run on a separate platform. In an example embodiment, the database may be accessible across the Internet. In several example embodiments, more than one database may be implemented.

In several example embodiments, a plurality of instructions stored on a computer readable medium may be executed by one or more processors to cause the one or more processors to carry out or implement in whole or in part the above-described operation of each of the above-described example embodiments of the system, the method, and/or any combination thereof. In several example embodiments, such a processor may include one or more of the microprocessor 1000a, any processor(s) that are part of the components of the system, and/or any combination thereof, and such a computer readable medium may be distributed among one or more components of the system. In several example embodiments, such a processor may execute the plurality of instructions in connection with a virtual computer system. In several example embodiments, such a plurality of instructions may communicate directly with the one or more processors, and/or may interact with one or more operating systems, middleware, firmware, other applications, and/or any combination thereof, to cause the one or more processors to execute the instructions.

The present disclosure introduces a fluid dispensing device that includes: a cartridge including a housing and a head coupled to the housing; wherein the housing forms a first chamber configured to accommodate a fluid; and wherein the head includes: a nozzle; and an elastomeric wall that is spaced from the nozzle to form a holding chamber; wherein the holding chamber is in fluid communication with the first chamber and configured to accommodate a portion of the fluid prior to ejection; wherein the nozzle forms one or more openings to eject the portion of the fluid from the holding chamber; and wherein the one or more openings form an oblong shape such that a length of the oblong shape is greater than a width of the oblong shape. In some embodiments, the device also includes an applicator sized to accommodate the cartridge; wherein the applicator includes an actuator movable between a loaded position and a striking position; wherein, when in the loaded position, the actuator is spaced from the elastomeric wall; and wherein, when in the striking position, the actuator has compressed the elastomeric wall toward the nozzle to eject the portion of the fluid from the holding chamber via the one or more openings. In some embodiments, the applicator further includes: a controller that controls the position of the actuator; and a blink detector that is operably coupled to the controller, wherein the blink detector includes a plurality of sensors; wherein each of the sensors includes a light-emitting diode to emit light onto a surface of an eye of a user and photodiode to detect reflection of the light emitted onto the surface of the eye; and wherein, based on the light detected by the photodiode of each sensor, the controller determines whether the user has blinked the eye. In some embodiments, the wavelength of light detected by the photodiode is from about 930 nm to about 950 nm. In some embodiments, the one or more openings include two parallel slots that together form the oblong shape. In some embodiments, the one or more openings include a plurality of openings arranged linearly to form the oblong shape. In some embodiments, a portion of the nozzle forming the one or more openings forms a concave internal surface and a convex external surface. In some embodiments, the elastomeric wall is movable between a first position relative to the one or more openings and a second position relative to the one or more openings; wherein, when in the first position, the elastomeric wall is spaced from the one or more openings; wherein, when in the second position, the elastomeric wall blocks the one or more openings; wherein moving the elastomeric wall from the first position to the second position ejects the fluid from the holding chamber; wherein, when in the second position, the elastomeric wall fluidically isolates the one or more openings from the first chamber; and wherein, when moving the elastomeric wall from the second position to the first position fluid is drawn from the first chamber into the holding chamber. In some embodiments, the applicator further includes an ultraviolet ("UV") light emitting diode positioned such that the UV light shines on at least a portion of the nozzle. In some embodiments, the UV light is between 265 nm and 285 nm; wherein the elastomeric wall includes a thermoelastic polymer including a thermo plastic vulcinate; and wherein the head forms an air entry port in fluid communication with the first chamber and further includes a sterile air filter that is welded to the head such that the sterile air filter filters the air passing through the air entry port.

The present disclosure also introduces a method of dispensing a viscous fluid from a fluid dispenser that includes a pair of light-emitting diodes and corresponding pair of photodiodes, a nozzle having one or more openings that form an oblong shape, a flexible membrane, a holding chamber positioned between the nozzle and the flexible membrane, a controller, and an actuator that is operably coupled to the controller, the method including: emitting light onto a surface of an eye using the pair of light-emitting diodes; detecting an amount of light reflecting from the surface of the eye using the pair of photodiodes; and actuating, using the controller and based on the amount of detected light, the actuator to depress the flexible membrane into the holding chamber thereby causing the viscous fluid to be ejected from the holding chamber through the one or more openings of the nozzle. In some embodiments, the method also includes shining ultraviolet ("UV") light from an UV light-emitting diode ("LED") onto a portion of the nozzle to sterilize the portion of the nozzle. In some embodiments, shining the UV light occurs for a predetermined period of time in response to the controller actuating the actuator. In some embodiments with optical proximity sensors for blink detection, the wavelength of light emitted by their LEDs and detected by the pair of photodiodes is from about 935 nm to about 945 nm. In some embodiments, the actuator includes an electromechanical solenoid. In some embodiments, the method also includes generating data regarding the actuation of the actuator; and communicating the data to a remote controller. In some embodiments, the oblong shape formed by the one or more openings has a length that is greater than a width; wherein the method further includes the controller determining that the length of the oblong shape is positioned generally parallel to the eyelids of the user based on the amount of light reflecting from the surface of the eye; and wherein ejecting the viscous fluid from the fluid dispenser is in response to the controller determining that the length of the oblong shape formed by the one or more openings is positioned generally parallel to the eyelids.

The present disclosure also introduces a method of dispensing one or more streams of viscous fluid on an eye of a user, the method including: accommodating the viscous fluid in a holding chamber of a cartridge, wherein the cartridge includes a nozzle having one or more openings that form an oblong shape, a flexible membrane, and wherein the holding chamber is positioned between the nozzle and the flexible membrane; and actuating a solenoid that depresses the flexible membrane to eject the one or more streams of the viscous fluid from the one or more openings at a velocity targeted between about 1.5 meters/second and about 3 meters/second; wherein the one or more openings form an oblong shape such that the one or more streams of the viscous fluid that is ejected from the holding chamber via the one or more openings form a sheet of the viscous fluid. In some embodiments, the one or more openings include two parallel slots with each slot having a length greater than a width of the slot; wherein the method further includes detecting alignment of the length of the slots with the eye of the user; and wherein actuating the solenoid is in response to detecting the alignment of the length of the slots with the eye of the user.

The phrase "at least one of A and B" should be understood to mean "A, B, or both A and B." The phrase "one or more of the following: A, B, and C" should be understood to mean "A, B, C, A and B, B and C, A and C, or all three of A, B, and C." The phrase "one or more of A, B, and C" should be understood to mean "A, B, C, A and B, B and C, A and C, or all three of A, B, and C."

Generally, any creation, storage, processing, and/or exchange of user data associated with the method, apparatus, and/or system disclosed herein is configured to comply with a variety of privacy settings and security protocols and prevailing data regulations, consistent with treating confidentiality and integrity of user data as an important matter. For example, the apparatus and/or the system may include a module that implements information security controls to comply with a number of standards and/or other agreements. In some embodiments, the module receives a privacy setting selection from the user and implements controls to comply with the selected privacy setting. In other embodiments, the module identifies data that is considered sensitive, encrypts data according to any appropriate and well-known method in the art, replaces sensitive data with codes to pseudonymize the data, and otherwise ensures compliance with selected privacy settings and data security requirements and regulations.

In several example embodiments, the elements and teachings of the various illustrative example embodiments may be combined in whole or in part in some or all of the illustrative example embodiments. In addition, one or more of the elements and teachings of the various illustrative example embodiments may be omitted, at least in part, and/or combined, at least in part, with one or more of the other elements and teachings of the various illustrative embodiments.

The term "about," as used herein, should generally be understood to refer to both numbers in a range of numerals. For example, "about 1 to 2" should be understood as "about 1 to about 2." Moreover, all numerical ranges herein should be understood to include each whole integer, or 1/10 of an integer, within the range.

Any spatial references such as, for example, "upper," "lower," "above," "below," "between," "bottom," "vertical," "horizontal," "angular," "upwards," "downwards," "side-to-side," "left-to-right," "right-to-left," "top-to-bottom," "bottom-to-top," "top," "bottom," "bottom-up," "top-down," etc., are for the purpose of illustration only and do not limit the specific orientation or location of the structure described above.

In several example embodiments, while different steps, processes, and procedures are described as appearing as distinct acts, one or more of the steps, one or more of the processes, and/or one or more of the procedures may also be performed in different orders, simultaneously, and/or sequentially. In several example embodiments, the steps, processes and/or procedures may be merged into one or more steps, processes, and/or procedures.

In several example embodiments, one or more of the operational steps in each embodiment may be omitted. Moreover, in some instances, some features of the present disclosure may be employed without a corresponding use of the other features. Moreover, one or more of the above-described embodiments and/or variations may be combined in whole or in part with any one or more of the other above-described embodiments and/or variations.

Although several example embodiments have been described in detail above, the embodiments described are examples only and are not limiting, and those skilled in the art will readily appreciate that many other modifications, changes, and/or substitutions are possible in the example embodiments without materially departing from the novel teachings and advantages of the present disclosure. Accordingly, all such modifications, changes, and/or substitutions are intended to be included within the scope of this disclosure as defined in the following claims.

In the claims, any means-plus-function clauses are intended to cover the structures described herein as performing the recited function and not only structural equivalents, but also equivalent structures. Moreover, it is the express intention of the applicant not to invoke 35 U.S.C. § 112(f) for any limitations of any of the claims herein, except for those in which the claim expressly uses the word "means" together with an associated function.

What is claimed is:

1. A fluid dispensing device, comprising:
    a cartridge comprising a housing and a head coupled to the housing,
    wherein the housing forms a first chamber configured to accommodate a fluid, and
    wherein the head comprises:
        a holding chamber in fluid communication with the first chamber and configured to accommodate a portion of the fluid prior to ejection;
        a moveable wall on a first side of the holding chamber; and
        a nozzle on a second side of the holding chamber opposite the moveable wall;
    wherein the nozzle forms one or more openings to eject the portion of the fluid from the holding chamber.

2. The device of claim 1, wherein the head is configured to be positioned in an actuator, wherein the actuator is movable between a loaded position and a striking position; wherein, when in the loaded position, the actuator is spaced from the moveable wall; and wherein, when in the striking position, the actuator has moved the moveable wall toward the nozzle to eject the portion of the fluid from the holding chamber via the one or more openings.

3. The device of claim 1, wherein the cartridge further comprises an actuatable cap, wherein the actuatable cap is configured to cover the nozzle in a closed position and is configured to uncover the nozzle in an open position, wherein the nozzle is in an open position when the fluid is dispensed from the nozzle.

4. The device of claim 3, wherein at least a portion of the actuatable cap is at least partially transparent to ultraviolet ("UV") light to allow, while in the actuatable cap is in the closed position, a portion of the UV light to illuminate the nozzle.

5. The device of claim 1, wherein the one or more openings comprise one of: a plurality of parallel slots or a plurality of openings arranged linearly.

6. The device of claim 1, wherein the one or more openings are arranged such that the portion of the fluid ejected has a width and a height, wherein the width is greater than or equal to the height.

7. The device of claim 6, wherein the one or more openings comprises a single oblong opening.

8. The device of claim 1, wherein:
the moveable wall is movable between a first position relative to the one or more openings and a second position relative to the one or more openings;
when in the first position, the moveable wall is spaced from the one or more openings;
when in the second position, the moveable wall blocks the one or more openings;
when moving the moveable wall from the first position to the second position ejects the fluid from the holding chamber;
when in the second position, the moveable wall fluidically isolates the one or more openings from the first chamber; and
when moving the moveable wall from the second position to the first position fluid is drawn from the first chamber into the holding chamber.

9. The device of claim 1, wherein the head forms an air entry port in fluid communication with the first chamber and further comprises a sterile air filter that is sealed to the head such that the sterile air filter filters the air passing through the air entry port, and wherein the sterile air filter is in the same plane as the moveable wall such that it can be sealed while sealing the moveable wall.

10. A fluid dispensing device, comprising:
a cartridge comprising:
a housing forming a first chamber configured to accommodate a fluid; and
a head coupled to the housing, the head comprising:
a holding chamber in fluid communication with the first chamber and configured to accommodate a portion of the fluid prior to ejection;
a moveable wall on a first part of the holding chamber; and
a nozzle on a second part of the holding chamber; and
an applicator configured to accommodate the cartridge, wherein the applicator comprises an actuator movable between a loaded position and a striking position,
wherein, when the actuator is in the loaded position, the moveable wall is in a first position relative to the nozzle, and
wherein, when the actuator is in the striking position, the moveable wall is in a second position which is closer to the nozzle than the first position.

11. The device of claim 10, wherein the applicator further comprises: a controller configured to control the position of the actuator; and a blink detector that is operably coupled to the controller, wherein the blink detector comprises a sensor; wherein the sensor comprises a light-emitting diode to emit light onto a surface of an eye of a user and photodiode to detect reflection of the light emitted onto the surface of the eye; and wherein, based on the light detected by the photodiode, the controller determines whether the user has blinked the eye.

12. The device of claim 11, wherein the light detected by the photodiode is infrared.

13. The device of claim 10, wherein the applicator further comprises an ultraviolet ("UV") light emitting diode positioned such that the UV light shines on at least a portion of the nozzle to sterilize a portion of the nozzle.

14. The device of claim 10, wherein the applicator further comprises a light source aligned with the nozzle, wherein the light source is visible when the nozzle is correctly aligned towards the eye.

15. The device of claim 10, wherein the one or more openings comprise one of: two parallel slots or a plurality of openings arranged linearly.

16. The device of claim 10, wherein, when in the first position, the moveable wall is spaced from the one or more openings; wherein, when in the second position, the moveable wall blocks the one or more openings; wherein, when in the second position, the moveable wall fluidically isolates the one or more openings from the first chamber; and wherein, when moving the moveable wall from the second position to the first position fluid is drawn from the first chamber into the holding chamber.

17. The device of claim 10, wherein the head forms an air entry port in fluid communication with the first chamber and further comprises a sterile air filter that is sealed to the head such that the sterile air filter filters the air passing through the air entry port, and wherein the sterile air filter is in the same plane as the moveable wall such that it can be sealed while sealing the moveable wall.

18. The device of claim 10, wherein the actuator comprises an electromechanical solenoid.

19. A method of dispensing a viscous fluid comprising the steps of:
providing a fluid dispenser comprising:
a cartridge comprising:
a housing forming a first chamber configured to accommodate a fluid; and
a head coupled to the housing, the head comprising:
a holding chamber in fluid communication with the first chamber and configured to accommodate a portion of the fluid prior to ejection;
a moveable wall on a first part of the holding chamber; and
a nozzle on a second part of the holding chamber opposite the moveable wall, wherein the nozzle forms one or more openings; and
an applicator sized to accommodate the cartridge, wherein the applicator comprises:
an actuator;
actuating the actuator to move the moveable wall thereby causing the portion of the fluid to be ejected from the holding chamber through the one or more openings of the nozzle.

* * * * *